(12) United States Patent
Hungenberg et al.

(10) Patent No.: US 9,872,494 B2
(45) Date of Patent: Jan. 23, 2018

(54) ACTIVE INGREDIENT COMBINATIONS COMPRISING PYRIDYLETHYLBENZAMIDES AND OTHER ACTIVE INGREDIENTS

(75) Inventors: Heike Hungenberg, Langenfeld (DE); Heiko Rieck, Burscheid (DE); Robert Masters, Vettweiss-Sievernich (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 13/990,586

(22) PCT Filed: Nov. 30, 2011

(86) PCT No.: PCT/EP2011/071418
§ 371 (c)(1),
(2), (4) Date: Sep. 18, 2013

(87) PCT Pub. No.: WO2012/072696
PCT Pub. Date: Jun. 7, 2012

(65) Prior Publication Data
US 2014/0005047 A1    Jan. 2, 2014

Related U.S. Application Data

(60) Provisional application No. 61/419,438, filed on Dec. 3, 2010.

(30) Foreign Application Priority Data

Dec. 1, 2010  (EP) .................................. 10193335

(51) Int. Cl.
| | | |
|---|---|---|
| *A01N 25/00* | (2006.01) | |
| *A01N 43/40* | (2006.01) | |
| *A01N 43/78* | (2006.01) | |
| *A01N 43/90* | (2006.01) | |
| *A01N 57/32* | (2006.01) | |
| *A01N 63/00* | (2006.01) | |
| *A01N 63/04* | (2006.01) | |
| *A01N 65/12* | (2009.01) | |

(52) U.S. Cl.
CPC ............. *A01N 43/40* (2013.01); *A01N 43/78* (2013.01); *A01N 43/90* (2013.01); *A01N 57/32* (2013.01); *A01N 63/00* (2013.01); *A01N 63/04* (2013.01); *A01N 65/12* (2013.01)

(58) Field of Classification Search
CPC ........ A01N 63/04; A01N 43/40; A01N 63/00; A01N 2300/00; A01N 51/00; C12R 1/79; C07D 213/02
USPC ........................................................ 424/405
See application file for complete search history.

(56) References Cited

U.S. PATENT DOCUMENTS

| | | | | |
|---|---|---|---|---|
| 5,051,255 A * | 9/1991 | Devidas et al. ......... | 424/195.15 |
| 5,215,747 A | 6/1993 | Hairston et al. | |
| 5,804,208 A | 9/1998 | Andersch et al. | |
| 5,989,543 A | 11/1999 | Davide et al. | |
| 6,150,406 A * | 11/2000 | Warrior et al. ............... | 514/477 |
| 6,994,849 B2 | 2/2006 | Droby et al. | |
| 7,572,818 B2 | 8/2009 | Mansfield et al. | |
| 7,786,148 B2 | 8/2010 | Gouot et al. | |
| 9,089,135 B2 * | 7/2015 | Andersch ............... | A01N 43/40 |
| 2005/0191279 A1 | 9/2005 | Selvig et al. | |
| 2005/0234110 A1 | 10/2005 | Mansfield et al. | |
| 2007/0105915 A1 | 5/2007 | Gouot et al. | |
| 2010/0130357 A1 | 5/2010 | Hungenberg et al. | |
| 2010/0249193 A1 * | 9/2010 | Andersch et al. ............ | 514/341 |
| 2016/0262391 A1 | 9/2016 | Hungenberg et al. | |

FOREIGN PATENT DOCUMENTS

| | | | | |
|---|---|---|---|---|
| CA | 2086351 A1 * | 7/1993 | ............. | A01N 63/00 |
| CA | 2205954 A1 | 6/1996 | | |
| CA | 2753150 A1 * | 9/2010 | ............. | A01N 25/00 |
| CN | 1053558(C) | * 6/2000 | | |
| CN | 101889583 A | 11/2010 | | |
| EP | 2039772 A2 | 3/2009 | | |
| EP | 2039772 A2 * | 3/2009 | ............. | A91N 43/40 |
| WO | WO 94/28725 A1 * | 12/1994 | ............. | A01N 63/04 |
| WO | 9505741 A1 | 3/1995 | | |
| WO | 2004016088 A2 | 2/2004 | | |
| WO | 2005077901 A1 | 8/2005 | | |
| WO | 2006107905 A1 | 10/2006 | | |
| WO | 2008003738 A1 | 1/2008 | | |
| WO | WO 2008/003738 A1 * | 1/2008 | | |
| WO | 2008092759 A2 | 8/2008 | | |
| WO | WO 2009/037242 A2 * | 3/2009 | ............. | A01N 63/00 |
| WO | WO 2009/124707 A2 * | 10/2009 | ............. | A01N 63/00 |
| WO | 2010108616 A1 | 9/2010 | | |
| WO | 2010108973 A2 | 9/2010 | | |
| WO | 2010128003 A2 | 11/2010 | | |
| WO | 2010130689 A1 | 11/2010 | | |

OTHER PUBLICATIONS

U.S. Appl. No. 12/731,812, filed Sep. 2010, Andersch et al.*
Bacillus-based Biofungicides as Seed Treatment (published online: Oct. 20, 2009).*
Biological Nematicide DiTera® ES (obtained online on Apr. 28, 2015 via www.kellysolutions.com (brochure: 2003).*
International Search Report for PCT/EP2011/071418 dated Mar. 5, 2010.
U.S. Appl. No. 13/256,346, filed Oct. 27, 2011.
U.S. Appl. No. 12/936,700, filed Jan. 3, 2011.
U.S. Appl. No. 14/577,476, filed Dec. 19, 2014.
Materials Entering Evaluation Process MEE vol. 2002-37 Oktober 2008 Biological Nematicide XP055298306.

* cited by examiner

*Primary Examiner* — Mina Haghighatian
*Assistant Examiner* — Helen Chui
(74) *Attorney, Agent, or Firm* — McBee Moore Woodward & Vanik IP, LLC

(57) ABSTRACT

The present invention relates to novel active ingredient combinations which consist of fluopyram and other known active ingredients and are very well suited for the control of animal pests, such as insects and/or unwanted acarids and/or nematodes, in foliar and soil application and/or in the treatment of seeds, and are also suitable for increasing yields.

11 Claims, No Drawings

ACTIVE INGREDIENT COMBINATIONS COMPRISING PYRIDYLETHYLBENZAMIDES AND OTHER ACTIVE INGREDIENTS

CROSS REFERENCE TO RELATED APPLICATIONS

This application is a §371 National Stage Application of PCT/EP2011/071418, filed Nov. 30, 2011, which claims priority to European Application No. 10193335.6, filed Dec. 1, 2010; and U.S. Provisional Application No. 61/419,438, filed Dec. 3, 2010.

BACKGROUND OF THE INVENTION

Field of the Invention

The present invention relates to new active ingredient combinations which consist of fluopyram and other known active ingredients and which are very well suited to the control of animal pests, such as insects and/or unwanted acarids and/or nematodes, in foliar and soil application and/or in seed treatment, and also to the boosting of yields.

Description of Related Art

It is already known that certain pyridylethylbenzamides possess fungicidal, insecticidal, and acaricidal and nematicidal properties.

WO 2004/016088 describes pyridylethylbenzamides and their use as fungacides. The possibility of combining one or more of the disclosed pyridylethylbenzamide derivatives with other known fungicides, insecticides, nematicides or acaricides for the purpose of broadening the spectrum of activity is likewise described. The application, however, teaches neither which insecticidal mixing partners are suitable, nor the mixing ratio in which insecticides and pyridylethylbenzamide derivatives are combined with one another. WO 2005/077901 teaches fungicidal compositions comprising at least one pyridylethylbenzamide, a fungicide and an inhibitor of electron transport in the respiratory chain of fungi. The patent application, however, does not mention any mixtures of pyridylethylbenzamides with insecticides. WO 2008/003738 teaches fungicidal compositions comprising at least one pyridylethylbenzamide and an insecticide. A possible nematicidal action of the compositions is described in the application, but not explicitly for mixtures comprising N-{2-[3-chloro-5-(trifluoromethyl)-2-pyridinyl]ethyl}-2-trifluoromethylbenzamide.

The activity of the active ingredients and active ingredient compositions described in the prior art is good, but is capable of improvement at low application rates in certain cases, especially in the context of nematode control.

SUMMARY

The object on which the present invention is based, therefore, is that of providing nematicidal, insecticidal and acaricidal active ingredient combinations having improved activity, especially with regard to nematodes.

It has now been found that active ingredient combinations comprising (1-1) N-{2-[3-chloro-5-(trifluoromethyl)-2-pyridinyl]ethyl}-2-trifluoromethylbenzamide of formula (I)

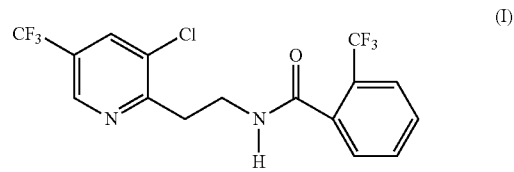 [SMILES: O=C(NCCc1ncc(C(F)(F)F)cc1Cl)c1ccccc1C(F)(F)F]

(fluopyram)
and also its N-oxides;
and
(II) at least one further active ingredient selected from the group consisting of fluensulfone (II-1), imicyafos (II-2), *Bacillus subtilis* (II-3), *Bacillus subtilis* strain QST 713 (Serenade™) (II-4), *Paecilomyces lilacinus* (II-5), *Paecilomyces lilacinus* strain 251 (Bioact™) (II-6), azadirachtin (II-7), thymol (II-8), *Metarhizium anisopliae* (II-9), *Rhizobium* spp. (II-10), *Beauveria* spp. (II-11), *Verticillium* spp. (II-12), *Metschnikowia fructicola* (II-13), *Metschnikowia fructicola* strain NRRL Y-30752. (II-14), *Bacillus subtilis* strain GB03 (II-15), *Bacillus pumilus* strain GB34 (II-16), *Bacillus pumilus* strain QST2808 (II-17), *Bacillus amyloliquefaciens* strain IN937a (II-18), *Bacillus amyloliquefaciens* strain FZB 42 (II-19), *Myrothecium verrucaria* strain AARC-0255 (II-20), pyrethrum (II-21), *Cydia pomonella* granulosis virus (CpGV) (II-22), *Metarhizium anisopliae* strain F52 (11-23), arbuscular *mycorrhiza* fungus (II-24), *Beauveria bassiana* strain ATCC 74040 (II-25), *Beauveria brongniartii* (II-26), *Lecanicillium lecanii* (also known as *Verticillium lecanii*) (II-27), *Bacillus thuringiensis* subsp. *tenebrionis* (II-28)
are very well suited to the control of phytopathogenic fungi and animal pests, more particularly nematodes, in foliar and soil application, particularly in the context of seed treatment, and also to the boosting of yields.

The insecticides or active nematicidal ingredients of group (II) are selected from the group consisting of the following:
fluensulfone (II-1) known from WO-A 2001/002378
and/or
imicyafos (II-2) known from EP-A 0464830
and/or
*Bacillus subtilis* (II-3)
and/or
*Bacillus subtilis* strain QST 713 (II-4)
and/or
*Paecilomyces lilacinus* (II-5)
and/or
*Paecilomyces lilacinus* strain 251 (II-6)
and/or
azadirachtin (Cas-No 11141-17-6) (II-7)
and/or
Thymol (II-8)
and/or
*Metarhizium anisopliae* (II-9),
and/or
*Rhizobium* spp. (II-10),
and/or
*Beauveria* spp. (II-11),
and/or
*Verticillium* spp (II-12)
and/or
*Metschnikowia fructicola* (II-13) known from Kurztman and Droby, System. Application Microbiol. (2001), 24, pp 395-399 and/or
*Metschnikowia fructicola* strain NRRL Y-30752, (II-14) known from U.S. Pat. No. 6,994,849
and/or
*Bacillus subtilis* strain GB03 (II-15) known under the name Kodiak™ marketed by Gustafson LLC and/or
*Bacillus pumilus* strain GB34 known under the name Yield-Shield™ marketed by Gustafson LLC
and/or
*Bacillus pumilus* strain QST2808 known under the name Sonata™ marketed by Agraquest
and/or
*Bacillus amyloliquefaciens* strain IN937a
and/or
*Myrothecium verrucaria* strain AARC-0255 known under the name DiTera™ marketed by Valent BioSciences
and/or
pyrethrum (II-21)
and/or
*Cydia pomonella* granulosis virus (CpGV) (II-22)
and/or
*Metarhizium anisopliae* strain F52 (II-23)
and/or
arbuscular *mycorrhiza* fungus (II-24)
and/or
*Beauveria bassiana* strain ATCC 74040 (known under the name Naturalis®) (II-25)
and/or
*Beauveria brongniartii* (II-26)
and/or
*Lecanicillium lecanii* (formerly known as *Verticillium lecanii*) (II-27)
and/or
*Bacillus thuringiensis* subsp. *tenebrionis* (11-28).

DETAILED DESCRIPTION OF A PREFERRED EMBODIMENT

In one preferred embodiment of the invention the active ingredients of group (II) are selected from the group consisting of fluensulfone (II-1), imicyafos (II-2), *Bacillus subtilis* (II-3), *Bacillus subtilis* strain QST 713 (Serenade™) (II-4), *Paecilomyces lilacinus* (II-5), *Paecilomyces lilacinus* strain 251 (Bioact™) (II-6), azadirachtin (II-7), thymol (II-8), *Metarhizium anisopliae* (II-9), *Rhizobium* spp. (II-10), *Beauveria* spp. (II-11), *Verticillium* spp. (II-12), *Metschnikowia fructicola* (II-13), *Metschnikowia fructicola* strain NRRL Y-30752. (II-14).

In one preferred embodiment of the invention the active ingredients of group (II) are selected from the group of bacteria consisting of *Bacillus subtilis* (II-3), *Bacillus subtilis* strain QST 713 (Serenade™) (II-4), *Bacillus subtilis* strain GB03 (II-15), *Bacillus pumilus* strain GB34 (II-16), *Bacillus pumilus* strain QST2808 (II-17), *Bacillus amyloliquefaciens* strain IN937a (II-18), *Rhizobium* spp. (II-10), *Bacillus thuringiensis* subsp. *tenebrionis* (II-28).

In one preferred embodiment of the invention the active ingredients of group (II) are selected from the group of *Bacillus* species consisting of *Bacillus subtilis* (II-3), *Bacillus subtilis* strain QST 713 (Serenade™) (II-4), *Bacillus subtilis* strain GB03 (II-15), *Bacillus pumilus* strain GB34 (II-16), *Bacillus pumilus* strain QST2808 (II-17), *Bacillus amyloliquefaciens* strain IN937a (II-18), *Bacillus thuringiensis* subsp. *tenebrionis* (II-28).

In one preferred embodiment of the invention the active ingredients of group (II) are selected from the group of fungal species consisting of *Paecilomyces lilacinus* (II-5), *Paecilomyces lilacinus* strain 251 (Bioact™) (II-6), *Metarhizium anisopliae* (II-9), *Beauveria* spp. (II-11), *Verticillium* spp. (II-12), *Metschnikowia fructicola* (II-13), *Metschnikowia fructicola* strain NRRL Y-30752. (II-14), *Myrothecium verrucaria* strain AARC-0255 (II-19), *Metarhizium anisopliae* strain F52 (II-23), arbuscular *mycorrhiza* fungus (II-24), *Beauveria bassiana*, in particular strain ATCC 74040 (II-25), *Beauveria brongniartii* (II-26), *Lecanicillium lecanii* (formerly known as *Verticillium lecanii*) (II-27).

In one preferred embodiment of the invention the active ingredients of group (II) are selected from the group consisting of fluensulfone (II-1), imicyafos (II-2), *Paecilomyces lilacinus* (II-5), *Paecilomyces lilacinus* strain 251 (Bioact™) (II-6), *Metarhizium anisopliae* (II-9), *Metschnikowia fructicola* (II-13), *Metschnikowia fructicola* strain NRRL Y-30752. (II-14), *Bacillus subtilis* strain GB03 (II-15), *Bacillus amyloliquefaciens* strain FZB 42 (II-19), *Bacillus thuringiensis* subsp. *tenebrionis* (II-28), pyrethrum (II-21), *Cydia pomonella* granulosis virus (CpGV) (II-22), *Metarhizium anisopliae* strain F52 (II-23), arbuscular *mycorrhiza* fungus (II-24).

In one preferred embodiment of the invention the active ingredients of group (II) are selected from the group consisting of fluensulfone (II-1), imicyafos (II-2), *Bacillus subtilis* (II-3), *Bacillus subtilis* strain QST 713 (Serenade™) (II-4), *Paecilomyces lilacinus* (II-5), *Paecilomyces lilacinus* strain 251 (Bioact™) (II-6) and also *Metschnikowia fructicola* (II-13).

In one particularly preferred embodiment of the invention the active ingredients of group (II) are selected from the group consisting of fluensulfone (II-1), imicyafos (II-2), *Bacillus subtilis* strain QST 713 (Serenade™) (II-4), *Paecilomyces lilacinus* strain 251 (Bioact™) (II-6).

In one preferred embodiment of the invention the active ingredients of group (II) are selected from the group of the low molecular mass active ingredients fluensulfone (II-1), imicyafos (II-2), azadirachtin (II-7), thymol (II-8).

Surprisingly, the fungicidal, insecticidal and/or acaricidal and/or nematicidal action, more particularly the nematicidal action, of the active ingredient combinations of the invention, particularly after soil application, is substantially higher than the sum of the actions of the individual active ingredients. The effect is an unpredictable true synergistic effect, and not merely a supplementation of action. Moreover, the active ingredient combinations of the invention are suitable for effecting a boost to yield.

Preferred active ingredient combinations are those comprising the compounds of the formula (I-1) and at least one active ingredient of the formula (II).

Of particular interest are the following combinations:
(I-1)+(II-1), (I-1)+(II-2), (I-1)+(II-3), (I-1)+(II-4), (I-1)+(II-5), (I-1)+(II-6), (I-1)+(II-7), (I-1)+(II-8), (I-1)+(II-9), (I-1)+(II-10), (I-1)+(II-11), (I-1)+(II-12), (I-1)+(II-13), (I-1)+(II-14), (I-1)+(II-15), (I-1)+(II-16), (I-1)+(II-17), (I-1)+(II-18), (I-1)+(II-19), (I-1)+(II-20), (I-1)+(II-21), (1-1)+(II-22), (I-1)+(II-23), (I-1)+(II-24), (I-1)+(II-25), (I-1)+(II-26), (I-1)+(II-27), (I-1)+(II-28).

The active ingredient combinations may also, furthermore, comprise other, admix components with fungicidal, acaricidal, nematicidal or insecticidal activity.

If the active ingredients are present in particular weight ratios in the active ingredient combinations of the invention, the improved action is apparent with particular clarity. However, within the active ingredient combinations, the weight ratios of the active ingredients can be varied within a relatively wide range. In general the combinations of the invention comprise active ingredients of the formula (I-1) and the mixing partner in the preferred and particularly preferred mixing ratios indicated in the table below:

| Mixing partner | Preferred mixing ratio (I-1):Mixing partner | Particularly preferred mixing ratio (I-1):Mixing partner | Very particularly preferred mixing ratio (I-1):Mixing partner |
| --- | --- | --- | --- |
| II-1 | 500:1 to 1:500 | 125:1 to 1:125 | 25:1 to 1:25 |
| II-2 | 500:1 to 1:500 | 125:1 to 1:125 | 25:1 to 1:25 |
| II-3 | 500:1 to 1:500 | 125:1 to 1:125 | 25:1 to 1:25 |
| II-4 | 500:1 to 1:500 | 125:1 to 1:125 | 25:1 to 1:25 |
| II-5 | 500:1 to 1:500 | 125:1 to 1:125 | 25:1 to 1:25 |
| II-6 | 500:1 to 1:500 | 125:1 to 1:125 | 25:1 to 1:25 |
| II-7 | 500:1 to 1:500 | 125:1 to 1:125 | 25:1 to 1:25 |
| II-8 | 500:1 to 1:500 | 125:1 to 1:125 | 25:1 to 1:25 |
| II-9 | 500:1 to 1:50000 | 125:1 to 1:12500 | 25:1 to 1:2500 |
| II-10 | 500:1 to 1:500 | 125:1 to 1:125 | 25:1 to 1:25 |
| II-11 | 500:1 to 1:500 | 125:1 to 1:125 | 25:1 to 1:25 |
| II-12 | 500:1 to 1:500 | 125:1 to 1:125 | 25:1 to 1:25 |
| II-13 | 500:1 to 1:500 | 125:1 to 1:125 | 25:1 to 1:25 |
| II-14 | 500:1 to 1:500 | 125:1 to 1:125 | 25:1 to 1:25 |
| II-15 | 500:1 to 1:500 | 125:1 to 1:125 | 25:1 to 1:25 |
| II-16 | 500:1 to 1:500 | 125:1 to 1:125 | 25:1 to 1:25 |
| II-17 | 500:1 to 1:500 | 125:1 to 1:125 | 25:1 to 1:25 |
| II-18 | 500:1 to 1:500 | 125:1 to 1:125 | 25:1 to 1:25 |
| II-19 | 500:1 to 1:500 | 125:1 to 1:125 | 25:1 to 1:25 |
| II-20 | 500:1 to 1:500 | 125:1 to 1:125 | 25:1 to 1:25 |
| II-21 | 500:1 to 1:500 | 125:1 to 1:125 | 25:1 to 1:25 |
| II-22 | 500:1 to 1:500 | 125:1 to 1:125 | 25:1 to 1:25 |
| II-23 | 500:1 to 1:500 | 125:1 to 1:125 | 25:1 to 1:25 |
| II-24 | 500:1 to 1:500 | 125:1 to 1:125 | 25:1 to 1:25 |
| II-25 | 500:1 to 1:500 | 125:1 to 1:125 | 25:1 to 1:25 |
| II-26 | 500:1 to 1:500 | 125:1 to 1:125 | 25:1 to 1:25 |
| II-27 | 500:1 to 1:500 | 125:1 to 1:125 | 25:1 to 1:25 |
| II-28 | 500:1 to 1:500 | 125:1 to 1:125 | 25:1 to 1:25 |

Animal Pests

The active ingredient combinations combine good tolerance by plants with suitability for controlling animal pests, such as insects and/or arachnids, and more particularly nematodes, which are prevalent in viticulture, fruit growing, agriculture, horticulture, and forestry. They can be used with preference as crop protection compositions. They are active against normally sensitive species and resistant species, and also against all or individual development stages. The aforementioned pests include the following:

Insects

Examples from the order of the Anoplura (*Phthiraptera*): *Damalinia* spp., *Haematopinus* spp., *Linognathus* spp., *Pediculus* spp., *Trichodectes* spp.

Examples from the class of the Arachnida: *Acarus* spp., *Aceria sheldoni*, *Aculops* spp., *Aculus* spp., *Amblyomma* spp., *Amphi tetranychus viennensis*, *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus mactans*, *Metatetranychus* spp., *Nuphersa* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

Examples from the class of the Bivalva: *Dreissena* spp.

Examples from the order of the Chilopoda: *Geophilus* spp., *Scutigera* spp.

Examples from the order of the Coleoptera: *Acalymma vittatum*, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Psylliodes* spp., *Ptinus* spp., *Rhizobius ventralis*, *Rhizopertha dominica*, *Sitophilus* spp., *Sphenophorus* spp., *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

Example from the order of the Collembola: *Onychiurus armatus*.

Example from the order of the Diplopoda: *Blaniulus guttulatus*.

Examples from the order of the Diptera: *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Cochliomyia* spp., *Contarinia* spp., *Cordylobia anthropophaga*, *Culex* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit*, *Pegomyia* spp., *Phorbia* spp., *Prodiplosis* spp., *Psila rosae*, *Rhagoletis* spp., *Stomoxys* spp., *Tabanus* spp., *Tannia* spp., *Tetanops* spp., *Tipula* spp.

Examples from the class of the Gastropoda: *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

Examples from the class of the helminths: *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp., *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp, *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is also possible for protozoa, such as Eimeria, to be controlled.

Examples from the order of the Heteroptera: *Anasa tristis*, *Antestiopsis* spp., *Blissus* spp., *Calocoris* spp., *Campy-*

*lomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

Examples from the order of the Homoptera: *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides Manus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

Examples from the order of the Hymenoptera: *Athalia* spp., *Diprion* spp., *Hoplocampa* spp., *Lasius* spp., *Monomorium pharaonis, Vespa* spp.

Examples from the order of the Isopoda: *Armadillidium vulgare, Oniscus asellus, Porcellio scaber.*

Examples from the order of the Isoptera: *Acromyrmex* spp., *Atta* spp., *Cornitermes cumulans, Microtermes obesi, Odontotermes* spp., *Reticulitermes* spp.

Examples from the order of the Lepidoptera: *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia kuehniella, Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantriai* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichoplusia* spp., *Tuta absoluta, Virachola* spp.

Examples from the order of the Orthoptera: *Acheta domesticus, Blatta orientalis, Blattella germanica, Dichroplus* spp., *Gryllotalpa* spp., *Leucophaea maderae, Locusta* spp., *Melanoplus* spp., *Periplaneta americana, Schistocerca gregaria.*

Examples from the order of Siphonaptera: *Ceratophyllus* spp., *Xenopsylla cheopis.*

Example from the order of the Symphyla: *Scutigerella* spp.

Examples from the order of the Thysanoptera: *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

Example from the order of the Thysanura: *Lepisma saccharina.*

Nematodes

All species of plant-parasitic nematodes may in principle be controlled using the active ingredient combinations of the invention. The active ingredient combinations of the invention prove particularly advantageous in the control of nematodes selected from the group consisting of the following: *Aglenchus agricola, Anguina tritici, Aphelenchoides arachidis, Aphelenchoides fragariae, Belonolaimus gracilis, Belonolaimus longicaudatus, Belonolaimus nortoni, Cacopaurus pestis, Criconemella curvata, Criconemella onoensis, Criconemella ornata, Criconemella rusium, Criconemella xenoplax* (=*Mesocriconema xenoplax*) and *Criconemella* spp. in general, *Criconemoides ferniae, Criconemoides onoense, Criconemoides ornatum* and *Criconemoides* spp. in general, *Ditylenchus destructor, Ditylenchus dipsaci, Ditylenchus myceliophagus* and *Ditylenchus* spp. in general, *Dolichodorus heterocephalus, Globodera pallida* (=*Heterodera pallida*), *Globodera rostochiensis, Globodera solanacearum, Globodera tabacum, Globodera virginiae, Helicotylenchus digonicus, Helicotylenchus dihystera, Helicotylenchus erythrine, Helicotylenchus multicinctus, Helicotylenchus nannus, Helicotylenchus pseudorobustus* and *Helicotylenchus* spp. in general, *Hemicriconemoides, Hemicycliophora arenaria, Hemicycliophora nudata, Hemicycliophora parvana, Heterodera avenae, Heterodera cruciferae, Heterodera glycines, Heterodera oryzae, Heterodera schachtii, Heterodera* zeae and *Heterodera* spp. in general, *Hoplolaimus aegyptii, Hoplolaimus californicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola* and *Longidorus* spp. in general, *Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne naasi, Meloidogyne paranaensis, Meloidogyne thamesi* and *Meloidogyne* spp. in general, *Meloinema* spp., *Nacobbus aberrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres* and *Paratrichodorus* spp. in general, *Paratylenchus hamatus, Paratylenchus minutus, Paratylenchus projectus* and *Paratylenchus* spp. in general, *Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae* and *Pratylenchus* spp. in general, *Pseudohalenchus minutus, Psilenchus magnidens, Psilenchus tumidus, Punctodera chalcoensis, Quinisulcius acutus, Radopholus citrophilus, Radopholus similis, Rotylenchulus borealis, Rotylenchulus parvus, Rotylenchulus reniformis* and *Rotylenchulus* spp. in general, *Rotylenchus laurentinus, Rotylenchus macrodoratus, Rotylenchus robustus, Rotylenchus uniformis* and *Rotylenchus* spp. in general, *Scutellonema brachyurum, Scutellonema bradys, Scutellonema clathricaudatum* and *Scutellonema* spp. in general, *Subanguina radiciola, Tetylenchus nicotianae, Trichodorus cylindricus, Trichodorus minor, Trichodorus primitivus, Trichodorus proximus, Trichodorus similis, Trichodorus sparsus* and *Trichodorus* spp. in general, *Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris* and *Tylenchorhynchus* spp. in general, *Tylenchulus semipenetrans, Xiphinema americanum, Xiphinema brevicolle, Xiphinema dimorphicaudatum, Xiphinema index* and *Xiphinema* spp. in general.

The active ingredient combinations of the invention prove especially advantageous in the control of nematodes selected from the group consisting of the following: *Meloidogyne* spp., such as *Meloidogyne incognita, Meloidogyne javanica, Meloidogyne hapla, Meloidogyne arenaria; Ditylenchus* ssp., such as *Ditylenchus dipsaci, Ditylelenchus destructor; Pratylenchus* ssp., such as *Pratylenchus penetrans, Pratylenchus fallax, Pratylenchus coffeae, Pratylenchus loosi, Pratylenchus vulnus; Globodera* spp., such as *Globodera rostochiensis, Globodera pallida* etc.; *Heterodera* spp., such as *Heterodera glycines Heterodera shachtoii* etc.; *Aphelenchoides* spp., such as *Aphelenchoides besseyi, Aphelenchoides ritzemabosi, Aphelenchoides fragarieae; Aphelenchus* ssp., such as *Aphelenchus avenae; Radopholus* ssp, such as *Radopholus similis; Tylenchulus* ssp., such as *Tylenchulus semipenetrans; Rotylenchulus* ssp., such as *Rotylenchulus reniformis;*
*Bursaphelenchus* spp., such as *Bursaphelenchus xylophilus, Aphelenchoides* spp., *Longidorus* spp., *Xiphinema* spp., *Trichodorus* spp.

Furthermore, the active ingredient combinations of the invention prove active in the control of nematodes which infect humans or animals, such as round worm, pin worm, filaria, *Wuchereri bancrofti*, thread worms (convoluted filaria), Gnathostoma etc.

Animal Health

The active ingredient combinations of the invention do not act only against plant, hygiene and stored-product pests but also in the veterinary sector, against animal parasites (ecto- and endoparasites) such as hard ticks, soft ticks, mange mites, leaf mites, flies (biting and licking), parasitic fly larvae, lice, hair lice, feather lice, and fleas. These parasites including the following:

Examples from the order of the Anoplurida: *Haematopinus* spp., *Linognathus* spp., *Pediculus* spp., *Phtirus* spp., *Solenopotes* spp.

Examples from the order of the Mallophagida and the suborders Amblycerina and Ischnocerina: *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

Examples from the order Diptera and the suborders Nematocerina and Brachycerina: *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

Examples from the order of the Siphonapterida: *Pulex* spp., *Ctenocephalides* spp., *Xenopsylla* spp., *Ceratophyllus* spp.

Examples from the order of the Heteropterida: *Cimex* spp., *Triatoma* spp., *Rhodnius* spp., *Panstrongylus* spp.

Examples from the order of the Blattarida: *Blatta orientalis, Periplaneta americana, Blattela germanica, Supella* spp.

Examples from the subclass of the Acari (Acarina) and from the orders of the Meta- and Mesostigmata: *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

Examples from the order of the Actinedida (Prostigmata) and Acaridida (Astigmata): *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active ingredient combinations of the invention are also suitable in the control of arthropods which infest agricultural livestock, such as cattle, sheep, goats, horses, pigs, donkeys, camels, buffalos, rabbits, chickens, turkeys, ducks, geese and bees, for example, other domesticated animals such as dogs, cats, caged birds and aquarium fish, for example, and also so-called experimentation animals, such as hamsters, guinea pigs, rats and mice, for example. The aim of controlling these arthropods is to reduce fatalities and yield reductions (of meat, milk, wool, hides, eggs, honey, etc.), so that more economic and easier animal husbandry is possible through the use of the active ingredient combinations of the invention.

Application of the active ingredient combinations of the invention in the veterinary sector and in animal husbandry is, in a conventional way, through enteral administration in the form of, for example, tablets, capsules, potions, drenches, granules, pastes, boluses, the feed-through method, and suppositories, and by parenteral administration, as for example through injections (intramuscular, subcutaneous, intravenous, intraperitoneal, etc.), implants, by nasal administration, by dermal application in the form, for example, of bathing or dipping, spraying, pour-on and spot-on, washing, and powdering, and also with the aid of molded articles containing active ingredient, such as collars, ear marks, tail marks, limb bands, halters, marking devices, etc.

In the context of application for livestock, poultry, domestic animals, etc., the active ingredient combinations may be applied as formulations (for example, powders, emulsions, flowable compositions) which comprise the active ingredients in an amount from 1 to 80 wt. %, directly or after 100- to 10 000-fold dilution, or may be used in the form of a chemical bath.

Crops

The crops to be protected, which have only been described in a general manner, are differentiated and specified below. Thus, with regard to use, vegetables are understood to mean, for example, fruit vegetables and flowerheads as vegetables, for example carrots, bell peppers, chilli peppers, tomatoes, aubergines, cucumbers, cucurbits, courgettes, broad beans, runner beans, bush beans, peas, artichokes, maize;

but also leafy vegetables, for example lettuce, chicory, endives, cress, rocket salad, field salad, iceberg lettuce, leek, spinach, swiss chard;

additionally tuber vegetables, root vegetables and stem vegetables, for example celeriac, beetroot, carrots, garden radish, horseradish, salsify, asparagus, table beet, palm shoots, bamboo shoots, and also bulb vegetables, for example onions, leek, fennel, garlic;

additionally *brassica* vegetables, such as cauliflower, broccoli, kohlrabi, red cabbage, white cabbage, green cabbage, savoy cabbage, brussels sprouts, chinese cabbage.

With regard to use, perennial crops are understood to mean citrus fruit, for example oranges, grapefruit, mandarins, lemons, limes, bitter oranges, kumquats, satsumas;

but also pome fruit, for example apples, pears and quince, and stone fruit, for example peaches, nectarines, cherries, plums, common plums, apricots;

additionally grapevine, hops, olives, tea, soya, oilseed rape, cotton, sugar cane, beet, potatoes, tobacco and tropical crops, for example mangoes, papayas, figs, pineapples, dates, bananas, durians, kakis, coconuts, cacao, coffee, avocados, lychees, maracujas, guavas, and also almonds and nuts, for example hazelnuts, walnuts, pistachios, cashew nuts, brazil nuts, pecan nuts, butter nuts, chestnuts, hickory nuts, macadamia nuts, peanuts, and additionally also soft fruit, for example blackcurrants, gooseberries, raspberries, blackberries, blueberries, strawberries, red bilberries, kiwis, cranberries.

With regard to use, ornamental plants are understood to mean annual and perennial plants, for example cut flowers, for example roses, carnations, gerbera, lilies, marguerites, chrysanthemums, tulips, daffodils, anemones, poppies, amaryllis, dahlias, azaleas, malves, but also, for example, bedding plants, potted plants and shrubs, for example roses, tagetes, pansies, geraniums, fuchsias, hibiscus, chrysanthemums, busy lizzies, cyclamen, african violets, sunflowers, begonias, in ornamental lawns, in golf lawns, but also in cereals such as barley, wheat, rye, triticale, oats, in rice, in millet, in maize, additionally, for example, bushes and conifers, for example fig trees, rhododendron, spruce trees, fir trees, pine trees, yew trees, juniper trees, stone pines, rose bays.

With regard to use, spices are understood to mean annual and perennial plants, for example aniseed, chilli pepper, bell pepper, pepper, vanilla, marjoram, thyme, cloves, juniper berries, cinnamon, tarragon, coriander, saffron, ginger.

The crops to be protected are highlighted in particular as follows: bell peppers, chilli peppers, tomatoes, aubergines, cucumbers, cucurbits, courgettes, artichokes, maize, celeriac, beetroot, carrots, garden radish, horseradish, salsifies, asparagus, table beet, palm shoots, bamboo shoots, onions, leek, oranges, grapefruit, mandarins, lemons, limes, bitter oranges, kumquats, satsumas, apples, pears, and quince, and stone fruit, such as, for example, peaches, nectarines, cherries, plums, common plums, apricots, grapevine, hops, soya, oilseed rape, cotton, sugar cane, beet, potatoes, tobacco, hazelnuts, walnuts, pistachios, cashew nuts, brazil nuts, pecan nuts, butter nuts, chestnuts, hickory nuts, macadamia nuts, peanuts, roses, carnations, gerbera, lilies, marguerites, chrysanthemums, tulips, daffodils, anemones, poppies, amaryllis, dahlias, azaleas, malves, barley, wheat, rye, triticale, oats, rice, millet, maize.

According to the invention, it is possible to treat all plants and plant parts. Plants are understood here to mean all plants and plant populations such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which can or cannot be protected by plant breeders' certificates.

GMOs

In a further preferred embodiment, transgenic plants and plant cultivars which have been obtained by genetic engineering methods, if appropriate in combination with conventional methods (Genetically Modified Organisms), and parts thereof are treated. The terms "parts" and "plant parts" have been explained above.

More preferably, plants of the plant cultivars which are in each case commercially available or in use are treated in accordance with the invention.

Depending on the plant species or plant cultivars, their location and growth conditions (soils, climate, vegetation period, nutrition), the treatment in accordance with the invention may also result in superadditive ("synergistic") effects. For example, reduced application rates and/or a widening of the activity spectrum and/or an increase in the activity of the substances and compositions which can be used in accordance with the invention, better plant growth, increased tolerance to high or low temperatures, increased tolerance to drought or to water or soil salt content, increased flowering performance, easier harvesting, accelerated maturation, higher harvest yields, better quality and/ or higher nutritional value of the harvested products, better storage qualities and/or processability of the harvested products are possible which exceed the effects which were actually to be expected.

According to the invention all plants and plant parts can be treated. By plants is meant all plants and plant populations such as desirable and undesirable wild plants, cultivars and plant varieties (whether or not protectable by plant varietal property or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts are meant all above-ground and below-ground parts and organs of plants such as shoot, leaf, blossom and root, where for example leaves, needles, stems, branches, flowers, fruiting bodies, fruits and seed and also roots, corms and rhizomes are listed. Crops and vegetative and generative propagating material, for example cuttings, corms, rhizones, runners and seeds, also belong to plant parts.

Among the plants that can be protected by the method according to the invention, mention may be made of major field crops such as maize, soya bean, cotton, *Brassica* oilseeds such as *Brassica napus* (e.g. canola), *Brassica rapa, B. juncea* (e.g. mustard) and *Brassica carinata*, rice, wheat, sugar beet, sugar cane, oats, rye, barley, millet, triticale, flax, vine and various fruits and vegetables of various botanical taxa such as Rosaceae sp. (for instance pome fruit such as apples and pears, but also stone fruit such as apricots, cherries, almonds and peaches, soft fruits such as strawberries), *Ribesioidae* sp., Juglandaceae sp., Betulaceae sp., Anacardiaceae sp., Fagaceae sp., Moraceae sp., Oleaceae sp., Actimidaceae sp., Lauraceae sp., Musaceae sp. (for instance banana trees and plantings), Rubiaceae sp. (for instance coffee), Theaceae sp., Sterculiceae sp., Rutaceae sp. (for instance lemons, oranges and grapefruit); Solanaceae sp. (for instance tomatoes, potatoes, peppers, eggplant), Liliaceae sp., Compositiae sp. (for instance lettuce, artichoke and chicory—including root chicory, endive or common chicory), Umbelliferae sp. (for instance carrot, parsley, celery and celeriac), Cucurbitaceae sp. (for instance cucumber—including pickling cucumber, squash, watermelon, gourds and melons), Alliaceae sp. (for instance onions and leek), Cruciferae sp. (for instance white cabbage, red cabbage, broccoli, cauliflower, brussel sprouts, pak Choi, kohlrabi, radish, horseradish, cress, Chinese cabbage), Leguminosae sp. (for instance peanuts, peas and beans—such as climbing beans and broad beans), Chenopodiaceae sp. (for instance Swiss chard, white cabbage spinach, beetroots), Malvaceae (for instance okra), Asparagaceae (for instance asparagus); horticultural and forest crops; ornamental plants; and also genetically modified homologs of these crops.

The method of treatment according to the invention can be used in the treatment of genetically modified organisms (GMOs), e.g. plants or seeds. Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using, for example, antisense technology, cosuppression technology or RNA interference—RNAi—technology). A heterologous gene that is located in the genome is also called a transgene. A transgene that is defined by its particular location in the plant genome is called a transformation event or transgenic event.

Depending on the plant species or plant cultivars, their location and growth conditions (soils, climate, vegetation period, nutrition), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage qualities and/or processability of the harvested products are possible, which exceed the effects which were actually to be expected.

At certain application rates, the active ingredient combinations according to the invention may also have a strengthening effect in plants. Accordingly, they are suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, also those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active ingredients.

Plants and plant cultivars which are preferably treated according to the invention include all plants which have genetic material which imparts particularly advantageous, useful traits to these plants (whether obtained by breeding and/or biotechnological means).

Plants and plant cultivars which are also preferably treated according to the invention are resistant against one or more biotic stresses, i.e. said plants show a better defense against animal and microbial pests, such as against nematodes, insects, mites, phytopathogenic fungi, bacteria, viruses and/or viroids.

For example, examples of nematode-resistant plants are described in U.S. patent application Ser. Nos. 11/765,491, 11/765,494, 10/926,819, 10/782,020, 12/032,479, 10/783, 417, 10/782,096, 11/657,964, 12/192,904, 11/396,808, 12/166,253, 12/166,239, 12/166,124, 12/166,209, 11/762, 886, 12/364,335, 11/763,947, 12/252,453, 12/209,354, 12/491,396 or 12/497,221.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, or shade avoidance.

Plants and plant cultivars which may also be treated according to the invention are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage qualities.

Examples of plants with the above-mentioned traits are non-exhaustively listed in table A.

Plants that may be treated according to the invention are hybrid plants that already express the characteristics of heterosis or hybrid vigor which results in generally higher yield and vigor, and improved health and resistance toward biotic and abiotic stresses. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in maize) be produced by detasseling, i.e. the mechanical removal of the male reproductive organs (or male flowers) but, more typically, male sterility is the result of genetic determinants in the plant genome. In that case, and especially when seeds are the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) have for example been described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289), or an eleusine EPSPS (WO 01/66704). It can also be a mutated EPSPS as described for example in EP 0837944, WO 00/66746, WO 00/66747 or WO 02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/036782, WO 03/092360, WO 05/012515 and WO 07/024,782. Glyphosate-tolerant plants can also be obtained by selecting plants containing naturally occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943,801 or 12/362,774. Plants comprising other genes that confer glyphosate tolerance, such as decarboxylase genes, are described in e.g. U.S. patent application Ser. Nos. 11/588,811, 11/185,342, 12/364,724, 11/185,560 or 12/423,926.

Other herbicide-resistant plants are for example plants that have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760, 602. One such efficient detoxifying enzyme is for example an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that have been made tolerant to the herbicides inhibiting the enzyme hydroxyphenylpyruvatedioxygenase (HPPD). HPPD is an enzyme that catalyses the reaction in which para-hydroxyphenylpyruvate (HPP) is transformed into homogentisate. Plants tolerant to HPPD-inhibitors can be transformed with a gene encoding a naturally occurring resistant HPPD enzyme, or a gene encoding a mutated or chimeric HPPD enzyme as described in WO 96/38567, WO 99/24585 and WO 99/24586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate dehydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide-resistant plants are plants that have been made tolerant to acetolactate synthase (ALS) inhibitors. Known ALS inhibitors include, for example, sulfonylurea, imidazolinone, triazolopyrimidine, pyrimidinyloxy (thio)benzoate and/or sulfonylaminocarbonyltriazolinone herbicides. Different mutations in the ALS enzyme (also known as acetohydroxy acid synthase, AHAS) are known to confer tolerance to different herbicides and groups of herbicides, as described for example in Tranel and Wright, Weed Science (2002), 50, 700-712), but also, in U.S. Pat. Nos. 5,605,011, 5,378,824, 5,141,870 and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351 and WO 2006/060634. Further sulfonylurea- and imidazolinone-tolerant plants are also described in for example WO 07/024,782 and U.S. patent application No. 61/288,958.

Other plants tolerant to imidazolinone and/or sulfonylurea can be obtained by induced mutagenesis, selection in cell cultures in the presence of the herbicide or mutation breeding as described for example for soya beans in U.S. Pat. No. 5,084,082, for rice in WO 97/41218, for sugar beet in U.S. Pat. No. 5,773,702 and WO 99/057965, for lettuce in U.S. Pat. No. 5,198,599 or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:
1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) in the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa or Cry3Bb or insecticidal portions thereof (e.g. EP-A 1999141 and WO 2007/107302), or such proteins encoded by synthetic genes as for example described in U.S. patent application Ser. No. 12/249,016; or
2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al., Nat. Biotechnol. (2001), 19, 668-72; Schnepf et al., Applied Environm. Microbiol. (2006), 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or
3) a hybrid insecticidal protein comprising parts of two different insecticidal crystal proteins from *Bacillus thuringiensis*, such as a hybrid of the proteins of 1) above or a hybrid of the proteins of 2) above, e.g. the Cry1A.105 protein produced by corn event MON89034 (WO 2007/027777); or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in corn events MON863 or MON88017, or the Cry3A protein in corn event MIR604; or
5) an insecticidal secreted protein *Bacillus thuringiensis* or from *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795) or
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT 102; or
9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. patent application Nos 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5); or
10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein).

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described for example in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of the poly(ADP-ribose) polymerase (PARP) gene in the plant cells or plants as described in WO 00/04173, WO/2006/045633, EP 04077984.5 or EP 06009836.5;
2) plants which contain a stress tolerance-enhancing transgene capable of reducing the expression and/or the activity of the PARG-encoding genes of the plants or plants cells, as described in e.g. WO 2004/090140;
3) plants which contain a stress tolerance-enhancing transgene encoding a plant-functional enzyme of the nicotinamide adenine dinucleotide salvage biosynthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in EP 04077624.7, WO 2006/133827, PCT/EP07/002,433, EP 1999263 or WO 2007/107326.

Plants or plant cultivars (obtained by plant biotechnology methods such as genetic engineering) which may also be treated according to the invention show altered quantity, quality and/or storage qualities of the harvested product and/or altered properties of specific constituents of the harvested product, such as:

1) transgenic plants which synthesize a modified starch, which in its physical-chemical characteristics, in particular the amylose content or the amylose/amylopectin ratio, the degree of branching, the average chain length, the side chain distribution, the viscosity behavior, the gelling strength, the starch grain size and/or the starch grain morphology, is changed in comparison with the synthesized starch in wild type plant cells or plants, so that this modified starch is better suited for special applications. Such transgenic plants synthesizing a modified starch are disclosed, for example in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026 and WO 97/20936.
2) Transgenic plants which synthesize non-starch carbohydrate polymers or which synthesize non-starch carbohydrate polymers with altered properties in comparison to wild type plants without genetic modification. Example are plants producing polyfructose, especially of the inulin and levan type, as disclosed in EP 0663956, WO 96/01904, WO 96/21023, WO 98/39460 and WO 99/24593, plants producing alpha-1,4-glucans as disclosed in WO 95/31553, US 2002031826, U.S. Pat. No. 6,284,479, U.S. Pat. No. 5,712,107, WO 97/47806, WO 97/47807, WO 97/47808 and WO 00/14249, plants producing alpha-1,6 branched alpha-1,4-glucans, as disclosed in WO 00/73422, and plants producing alternan, as disclosed in WO 00/47727, WO 00/73422, EP 06077301.7, U.S. Pat. No. 5,908,975 and EP 0728213.
3) Transgenic plants which produce hyaluronan, as for example disclosed in WO 2006/032538, WO 2007/039314, WO 2007/039315, WO 2007/039316, JP 2006304779 and WO 2005/012529.
4) Transgenic plants or hybrid plants, such as onions with characteristics such as 'high soluble solids content', 'low pungency' (LP) and/or 'long storage' (LS), as described in U.S. patent application Ser. Nos. 12/020,360 and 61/054,026.

Plants or plant cultivars (that have been obtained by plant biotechnology methods such as genetic engineering) which may also be treated according to the invention are plants, such as cotton plants, with altered fiber characteristics. Such plants can be obtained by genetic transformation, or by selection of plants which contain a mutation imparting such altered fiber characteristics and include:

a) plants, such as cotton plants, containing an altered form of cellulose synthase genes as described in WO 98/00549,
b) plants, such as cotton plants, containing an altered form of rsw2 or rsw3 homologous nucleic acids as described in WO 2004/053219;
c) plants, such as cotton plants, with increased expression of sucrose phosphate synthase as described in WO 01/17333;
d) plants, such as cotton plants, with increased expression of sucrose synthase as described in WO 02/45485;
e) plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or in U.S. patent application No. 61/128,938;
f) plants, such as cotton plants, having fibers with altered reactivity, e.g. through the expression of N-acetylglucosamintransferase gene including nodC and chitin synthase genes as described in WO 2006/136351.

Plants or plant cultivars (that have been obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants which contain a mutation imparting such altered oil characteristics and include:

a) plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947;

b) plants such as oilseed rape plants, producing oil having a low linolenic acid content as described in U.S. Pat. No. 6,270,828, U.S. Pat. No. 6,169,190 or U.S. Pat. No. 5,965,755.

c) Plants such as oilseed rape plants, producing oil having a low level of saturated fatty acids as described e.g. in U.S. Pat. No. 5,434,283 or U.S. patent application Ser. No. 12/668,303.

Plants or plant cultivars (that have been obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants which contain a mutation imparting such altered seed shattering characteristics and include plants such as oilseed rape plants with delayed or reduced seed shattering as described in U.S. patent application No. 61/135,230, WO09/068,313 and WO10/006,732.

Particularly useful transgenic plants which may be treated according to the invention are plants containing transformation events, or combinations of transformation events, that are the subject of petitions for non-regulated status, in the United States of America, to the Animal and Plant Health Inspection Service (APHIS) of the United States Department of Agriculture (USDA), whether such petitions are granted or are still pending. At any time this information is readily available from APHIS (4700 River Road, Riverdale, Md. 20737, USA), for instance on its interne site (URL http://www.aphis.usda.gov/brs/notreg.html). On the filing date of this application the petitions for non-regulated status that were pending with APHIS or granted by APHIS were those listed in table B which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of a petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as line or lines) for which non-regulated status is requested.

APHIS documents: various documents published by APHIS in relation to the petition and which can be requested from APHIS.

Additionally particularly useful plants containing single transformation events or a combination of transformation events are listed for example in the database from various national or regional regulatory agencies (see for example http://gmoinfo.jrc.it/gmp_browse.aspx and http://ceragm-c.org/index.php?evidcode=&hstIDXCode=&gType=&AbbrCode=&atCode=&stCode=&coIDCode=&action=gm_crop_database&mode=Submit).

Further particular transgenic plants include plants containing a transgene in an agronomically neutral or beneficial position as described in any of the patent publications listed in table C.

In one embodiment of the invention the plants A-1 to A-183 of table A, in total or in part, or propagation material of said plants, is treated or contacted with the active ingredient combinations of the invention, alone or in the form of compositions comprising an active ingredient combination.

| No. | Transgenic event | Company | Description | Crop |
|---|---|---|---|---|
| A-1 | ASR368 | Scotts Seeds | Glyphosate tolerance derived by inserting a modified 5-enolpyruvylshikimate-3-phosphate synthase (EPSPS) encoding gene from *Agrobacterium tumefaciens*, parent line B99061. | *Agrostis stolonifera* Creeping bentgrass |
| A-2 | Asr-368 | | Glyphosate tolerance; US 2006-162007 | bentgrass |
| A-3 | H7-1 | Monsanto Company | Glyphosate herbicide tolerant sugar beet produced by inserting a gene encoding the enzyme 5-enolypyruvylshikimate-3-phosphate synthase (EPSPS) from the CP4 strain of *Agrobacterium tumefaciens*; WO 2004-074492 | *Beta vulgaris* |
| A-4 | T120-7 | Bayer Crop-Science (Aventis Crop-Science (AgrEvo)) | Introduction of the PPT-acetyltransferase (PAT) encoding gene from *Streptomyces viridochromogenes*, an aerobic soil bacterium. PPT normally acts to inhibit glutamine synthetase, causing a fatal accumulation of ammonia. Acetylated PPT is inactive. | *Beta vulgaris* |
| A-5 | GTSB77 | Novartis Seeds; Monsanto Company | Glyphosate herbicide tolerant sugar beet produced by inserting a gene encoding the enzyme 5-enolypyruvylshikimate-3-phosphate synthase (EPSPS) from the CP4 strain of *Agrobacterium tumefaciens*. | *Beta vulgaris* (sugar beet) |
| A-6 | T227-1 | | Glyphosate tolerance; US 2004-117870 | *Beta vulgaris* sugar beet |
| A-7 | 23-18-17, 23-198 | Monsanto Company (formerly Calgene) | High laurate acid (12:0) and myristate acid (14:0) canola produced by inserting a thioesterase encoding gene from the California bay laurel (*Umbellularia californica*). | *Brassica napus* (Argentine Canola) |
| A-8 | 45A37, 46A40 | Pioneer Hi-Bred International Inc. | High oleic acid and low linolenic acid canola produced through a combination of chemical mutagenesis to select for a fatty acid desaturase mutant with elevated oleic acid content, and traditional back-crossing to introduce the low linolenic acid trait. | *Brassica napus* (Argentine Canola) |

| No. | Transgenic event | Company | Description | Crop |
|---|---|---|---|---|
| A-9 | 46A12, 46A16 | Pioneer Hi-Bred International Inc. | Combination of chemical mutagenesis, to achieve the high oleic acid trait, and traditional breeding with registered canola varieties. | Brassica napus (Argentine Canola) |
| A-10 | GT200 | Monsanto Company | Glyphosate herbicide tolerant canola produced by inserting genes encoding the enzymes 5-enolypyruvylshikimate-3-phosphate synthase (EPSPS) from the CP4 strain of Agrobacterium tumefaciens and glyphosate oxidase from Ochrobactrum anthropi. | Brassica napus (Argentine Canola) |
| A-11 | GT73, RT73 | Monsanto Company | Glyphosate herbicide tolerant canola produced by inserting genes encoding the enzymes 5-enolypyruvylshikimate-3-phosphate synthase (EPSPS) from the CP4 strain of Agrobacterium tumefaciens and glyphosate oxidase from Ochrobactrum anthropi. | Brassica napus (Argentine Canola) |
| A-12 | HCN10 | Aventis CropScience | Introduction of the PPT-acetyltransferase (PAT) encoding gene from Streptomyces viridochromogenes, an aerobic soil bacterium. PPT normally acts to inhibit glutamine synthetase, causing a fatal accumulation of ammonia. Acetylated PPT is inactive. | Brassica napus (Argentine Canola) |
| A-13 | HCN92 | Bayer Crop-Science (Aventis CropScience (AgrEvo)) | Introduction of the PPT-acetyltransferase (PAT) encoding gene from Streptomyces viridochromogenes, an aerobic soil bacterium. PPT normally acts to inhibit glutamine synthetase, causing a fatal accumulation of ammonia. Acetylated PPT is inactive. | Brassica napus (Argentine Canola) |
| A-14 | MS1, RF1 => PGS1 | Aventis CropScience (formerly Plant Genetic Systems) | Male sterility, fertility restoration, pollination control system displaying glufosinate herbicide tolerance. MS lines contained the barnase gene from Bacillus amyloliquefaciens, RF lines contained the barstar gene from the same bacterium, and both lines contained the phosphinothricin N-acetyltransferase (PAT) encoding gene from Streptomyces hygroscopicus. | Brassica napus (Argentine Canola) |
| A-15 | MS1, RF2 => PGS2 | Aventis CropScience (formerly Plant Genetic Systems) | Male sterility, fertility restoration, pollination control system displaying glufosinate herbicide tolerance. MS lines contained the barnase gene from Bacillus amyloliquefaciens, RF lines contained the barstar gene from the same bacterium, and both lines contained the phosphinothricin N-acetyltransferase (PAT) encoding gene from Streptomyces hygroscopicus. | Brassica napus (Argentine Canola) |
| A-16 | MS8 × RF3 | Bayer CropScience (Aventis CropScience (AgrEvo)) | Male sterility, fertility restoration, pollination control system displaying glufosinate herbicide tolerance. MS lines contained the barnase gene from Bacillus amyloliquefaciens, RF lines contained the barstar gene from the same bacterium, and both lines contained the phosphinothricin N-acetyltransferase (PAT) encoding gene from Streptomyces hygroscopicus. | Brassica napus (Argentine Canola) |
| A-17 | MS-B2 | | Male sterility, WO 01/31042 | Brassica napus (Argentine Canola) |
| A-18 | MS-BN1/RF-BN1 | | Male sterility/restoration; WO 01/41558 | Brassica napus (Argentine Canola) |
| A-19 | NS738, NS1471, NS1473 | Pioneer Hi-Bred International Inc. | Selection of somaclonal variants with altered acetolactate synthase (ALS) enzymes, following chemical mutagenesis. Two lines (P1, P2) were initially selected with modifications at different unlinked loci. NS738 contains the P2 mutation only. | Brassica napus (Argentine Canola) |
| A-20 | OXY-235 | Aventis CropScience (formerly Rhône Poulenc Inc.) | Tolerance to the herbicides bromoxynil and ioxynil by incorporation of the nitrilase gene from Klebsiella pneumoniae. | Brassica napus (Argentine Canola) |
| A-21 | PHY14, PHY35 | Aventis CropScience (formerly Plant Genetic Systems) | Male sterility was obtained via insertion of the barnase ribonuclease gene from Bacillus amyloliquefaciens; fertility restoration by insertion of the barstar RNase inhibitor; PPT resistance via PPT-acetyltransferase (PAT) from Streptomyces hygroscopicus. | Brassica napus (Argentine Canola) |
| A-22 | PHY36 | Aventis CropScience (formerly Plant Genetic Systems) | Male sterility was obtained via insertion of the barnase ribonuclease gene from Bacillus amyloliquefaciens; fertility restoration by insertion of the barstar RNase inhibitor; PPT-acetyltransferase (PAT) from Streptomyces hygroscopicus. | Brassica napus (Argentine Canola) |
| A-23 | RT73 | | Glyphosate resistance; WO 02/36831 | Brassica napus (Argentine Canola) |

| No. | Transgenic event | Company | Description | Crop |
|---|---|---|---|---|
| A-24 | T45 (HCN28) | Bayer CropScience (Aventis CropScience (AgrEvo)) | Introduction of the PPT-acetyltransferase (PAT) encoding gene from *Streptomyces viridochromogenes*, an aerobic soil bacterium. PPT normally acts to inhibit glutamine synthetase, causing a fatal accumulation of ammonia. Acetylated PPT is inactive. | *Brassica napus* (Argentine Canola) |
| A-25 | HCR-1 | Bayer Crop Science (Aventis CropScience (AgrEvo)) | Introduction of the glufosinate ammonium herbicide tolerance trait from transgenic *B. napus* line T45. This trait is imparted by the gene for phosphinothricin acetyltransferase (PAT) from *S. viridochromogenes*. | *Brassica rapa* (Polish Canola) |
| A-26 | ZSR500/502 | Monsanto Company | Introduction of a modified 5-enol-pyruvylshikimate-3-phosphate synthase (EPSPS) and a gene from *Achromobacter* sp., that degrades glyphosate by conversion to aminomethylphosphonic acid (AMPA) and glyoxylate by interspecific crossing with GT73. | *Brassica rapa* (Polish Canola) |
| A-27 | EE-1 | | Insect resistance (Cry1Ac); WO 2007/091277 | aubergine |
| A-28 | 55-1/63-1 | Cornell University | Papaya ringspot virus (PRSV)-resistant papaya produced by inserting the coat protein (CP)-encoding sequences from this plant potyvirus. | *Carica papaya* (papaya) |
| A-29 | RM3-3, RM3-4, RM3-6 | Bejo Zaden BV | Male sterility was obtained via insertion of the barnase ribonuclease gene from *Bacillus amyloliquefaciens*; PPT resistance was obtained via the bar gene from S. hygroscopicus, which encodes the PAT enzyme. | *Cichorium intybus* (chicory) |
| A-30 | A, B | Agritope Inc. | Reduced accumulation of 5-adenosylmethionine (SAM), and consequently reduced ethylene synthesis, by introduction of the gene encoding 5-adenosylmethionine hydrolase. | *Cucumis melo* (melon) |
| A-31 | CZW-3 | Asgrow (USA); Seminis Vegetable Inc. (Canada) | Cucumber mosaic virus (CMV)-, zucchini yellows mosaic virus (ZYMV)- and watermelon mosaic virus (WMV) 2-resistant squash (*Curcurbita pepo*) produced by inserting the coat protein (CP)-encoding sequences from each of these plant viruses into the host genome. | *Cucurbita pepo* (squash) |
| A-32 | ZW20 | Upjohn (USA); Seminis Vegetable Inc. (Canada) | Zucchini yellows mosaic (ZYMV)- and watermelon mosaic virus (WMV) 2-resistant squash (*Curcurbita pepo*) produced by inserting the coat protein (CP)-encoding sequences from each of these plant potyviruses into the host genome. | *Cucurbita pepo* (squash) |
| A-33 | 66 | Florigene Pty Ltd. | Delayed senescence and sulfonylurea herbicide-tolerant carnations produced by inserting a truncated copy of the carnation aminocyclopropane cyclase (ACC) synthase encoding gene in order to suppress expression of the endogenous unmodified gene, which is required for normal ethylene biosynthesis. Tolerance to sulfonylurea herbicides was obtained via the introduction of a chlorosulfuron-tolerant version of the acetolactate synthase (ALS)-encoding gene from tobacco. | *Dianthus caryophyllus* (carnation) |
| A-34 | 4, 11, 15, 16 | Florigene Pty Ltd. | Modified color and sulfonylurea herbicide-tolerant carnations produced by inserting two anthocyanin biosynthetic genes whose expression results in a violet/mauve coloration. Tolerance to sulfonylurea herbicides was obtained via the introduction of a chlorosulfuron-tolerant version of the acetolactate synthase (ALS)-encoding gene from tobacco. | *Dianthus caryophyllus* (carnation) |
| A-35 | 959A, 988A, 1226A, 1351A, 1363A, 1400A | Florigene Pty Ltd. | Introduction of two anthocyanin biosynthetic genes which results in a violet/mauve coloration; introduction of a variant form of acetolactate synthase (ALS). | *Dianthus caryophyllus* (carnation) |
| A-36 | 3560.4.3.5 | | Glyphosate/ALS inhibitor-tolerance; WO 2008002872 | *Glycine max* L. (soya bean) |
| A-37 | A2704-12 | | Glufosinate tolerance; WO 2006/108674 | *Glycine max* L. (soya bean) |
| A-38 | A2704-12, A2704-21, A5547-35 | Aventis CropScience | Glufosinate ammonium herbicide-tolerant soya bean produced by inserting a modified phosphinothricin acetyltransferase (PAT)-encoding gene from the soil bacterium *Streptomyces viridochromogenes*. | *Glycine max* L. (soya bean) |
| A-39 | A5547-127 | Bayer CropScience (Aventis CropScience (AgrEvo)) | Glufosinate ammonium herbicide-tolerant soya bean produced by inserting a modified phosphinothricin acetyltransferase (PAT)-encoding gene from the soil bacterium *Streptomyces viridochromogenes*. | *Glycine max* L. (soya bean) |
| A-40 | A5547-35 | | Glufosinate tolerance; WO 2006/108675 | *Glycine max* L. (soya bean) |

| No. | Transgenic event | Company | Description | Crop |
|---|---|---|---|---|
| A-41 | DP-305423-1 | | High oleic acid content/ALS inhibitor tolerance; WO 2008/054747 | *Glycine max* L. (soya bean) |
| A-42 | DP356043 | Pioneer Hi-Bred International Inc. | Soya bean event with two herbicide tolerance genes: glyphosate N-acetyltransferase, which detoxifies glyphosate, and a modified acetolactate synthase (A | *Glycine max* L. (soya bean) |
| A-43 | G94-1, G94-19, G168 | DuPont Canada Agricultural Products | High oleic acid soya bean produced by inserting a second copy of the fatty acid desaturase (GmFad2-1) encoding gene from soya bean, which resulted in "silencing" of the endogenous host gene. | *Glycine max* L. (soya bean) |
| A-44 | GTS 40-3-2 | Monsanto Company | Glyphosate-tolerant soya bean variety produced by inserting a modified 5-enolpyruvylshikimate-3-phosphate synthase (EPSPS)-encoding gene from the soil bacterium *Agrobacterium tumefaciens*. | *Glycine max* L. (soya bean) |
| A-45 | GU262 | Bayer CropScience (Aventis CropScience (AgrEvo)) | Glufosinate ammonium herbicide-tolerant soya bean produced by inserting a modified phosphinothricin acetyltransferase (PAT)-encoding gene from the soil bacterium *Streptomyces viridochromogenes*. | *Glycine max* L. (soya bean) |
| A-46 | MON87701 | | Insect resistance (Cry1Ac); WO 2009064652 | *Glycine max* L. (soya bean) |
| A-47 | MON87705 | | altered fatty acid levels (mid-oleic acid and low saturated); WO 2010037016 | *Glycine max* L. (soya bean) |
| A-48 | MON87754 | | Increased oil content; WO 2010024976 | *Glycine max* L. (soya bean) |
| A-49 | MON87769 | | Stearidonic acid (SDA)-comprising oil; WO 2009102873 | *Glycine max* L. (soya bean) |
| A-50 | MON89788 | Monsanto Company | Glyphosate-tolerant soya bean variety produced by inserting a modified 5-enolpyruvylshikimate-3-phosphate synthase (EPSPS)-encoding aroA (epsps) gene from *Agrobacterium tumefaciens* CP4; WO 2006130436 | *Glycine max* L. (soya bean) |
| A-51 | OT96-15 | Agriculture & Agri-Food Canada | Low linolenic acid soya bean produced through traditional cross-breeding to incorporate the novel trait from a naturally occurring fan1 gene mutant that was selected for low linolenic acid content. | *Glycine max* L. (soya bean) |
| A-52 | W62, W98 | Bayer CropScience (Aventis CropScience (AgrEvo)) | Glufosinate ammonium herbicide-tolerant soya bean produced by inserting a modified phosphinothricin acetyltransferase (PAT)-encoding gene from the soil bacterium *Streptomyces hygroscopicus*. | *Glycine max* L. (soya bean) |
| A-53 | 15985 | Monsanto Company | Insect-resistant cotton derived by transformation of the DP50B parent variety, which contained event 531 (expressing Cry1Ac protein), with purified plasmid DNA containing the cry2Ab- gene from *B. thuringiensis* subsp. kurstaki. | *Gossypium hirsutum* L. (cotton) |
| A-54 | 1143-14A | | Insect resistance (Cry1Ab); WO 2006/128569 | *Gossypium hirsutum* L. (cotton) |
| A-55 | 1143-51B | | Insect resistance (Cry1Ab); WO 2006/128570 | *Gossypium hirsutum* L. (cotton) |
| A-56 | 19-51A | DuPont Canada Agricultural Products | Introduction of a variant form of acetolactate synthase (ALS). | *Gossypium hirsutum* L. (cotton) |
| A-57 | 281-24-236 | DOW AgroSciences LLC | Insect-resistant cotton produced by inserting the cry1F gene from *Bacillus thuringiensisvar*. aizawai. The PAT-encoding gene from *Streptomyces viridochromogenes* was introduced as a selectable marker. | *Gossypium hirsutum* L. (cotton) |
| A-58 | 3006-210-23 | DOW AgroSciences LLC | Insect-resistant cotton produced by inserting the cry1Ac gene from *Bacillus* thuringiensissubsp. kurstaki. The PAT-encoding gene from *Streptomyces viridochromogenes* was introduced as a selectable marker. | *Gossypium hirsutum* L. (cotton) |
| A-59 | 31807/31808 | Calgene Inc. | Insect-resistant bromoxynil herbicide-tolerant cotton produced by inserting the cry1Ac gene from *Bacillus thuringiensis* and a nitrilase-encoding gene from *Klebsiella pneumoniae*. | *Gossypium hirsutum* L. (cotton) |
| A-60 | BXN | Calgene Inc. | Bromoxynil herbicide-tolerant cotton produced by inserting a nitrilase-encoding gene from *Klebsiella pneumoniae*. | *Gossypium hirsutum* L. (cotton) |

| No. | Transgenic event | Company | Description | Crop |
|---|---|---|---|---|
| A-61 | CE43-67B | | Insect resistance (Cry1Ab); WO 2006/128573 | Gossypium hirsutum L. (cotton) |
| A-62 | CE44-69D | | Insect resistance (Cry1Ab); WO 2006/128571 | Gossypium hirsutum L. (cotton) |
| A-63 | CE46-02A | | Insect resistance (Cry1Ab); WO 2006/128572 | Gossypium hirsutum L. (cotton) |
| A-64 | Cot102 | | Insect resistance (Vip3A); US 2006-130175 | Gossypium hirsutum L. (cotton) |
| A-65 | COT102 | Syngenta Seeds, Inc. | Insect-resistant cotton produced by inserting the vip3A(a) gene from Bacillus thuringiensis AB88. The APH4-encoding gene from E. coli was introduced as a selectable marker. | Gossypium hirsutum L. (cotton) |
| A-66 | COT202 | | Insect resistance (VIP3A); US2009181399 | Gossypium hirsutum L. (cotton) |
| A-67 | Cot202 | | Insect resistance (VIP3); US 2007-067868 | Gossypium hirsutum L. (cotton) |
| A-68 | DAS-21Ø23-5 × DAS-24236-5 | DOW AgroSciences LLC | WideStrike ™, a stacked insect-resistant cotton derived from conventional cross-breeding of parental lines 3006-210-23 (OECD identifier: DAS-21Ø23-5) and 281-24-236 (OECD identifier: DAS-24236-5). | Gossypium hirsutum L. (cotton) |
| A-69 | DAS-21Ø23-5 × DAS-24236-5 × MON88913 | DOW AgroSciences LLC und Pioneer Hi-Bred International Inc. | Stacked insect-resistant and glyphosate-tolerant cotton derived from conventional cross-breeding of WideStrike cotton (OECD identifier: DAS-21Ø23-5 x DAS-24236-5) with MON88913, known as RoundupReady Flex (OECD identifier: MON-88913-8). | Gossypium hirsutum L. (cotton) |
| A-70 | DAS-21Ø23-5 × DAS-24236-5 × MON-Ø1445-2 | DOW AgroSciences LLC | WideStrike ™/Roundup Ready ® cotton, a stacked insect-resistant and glyphosate-tolerant cotton derived from conventional cross-breeding of WideStrike cotton (OECD identifier: DAS-21Ø23-5 x DAS-24236-5) with MON1445 (OECD identifier: MON-Ø1445-2). | Gossypium hirsutum L. (cotton) |
| A-71 | EE-GH3 | | Glyphosate tolerance; WO 2007/017186 | Gossypium hirsutum L. (cotton) |
| A-72 | EE-GH5 | | Insect resistance (Cry1Ab); WO 2008/122406 | Gossypium hirsutum L. (cotton) |
| A-73 | EE-GH6 | | Insect resistance (cry2Ae); W02008151780 | Gossypium hirsutum L. (cotton) |
| A-74 | event 236 | 281-24- | Insect resistance (Cry1F); WO 2005/103266 | Gossypium hirsutum L. (cotton) |
| A-75 | event3006-210-23 | | Insect resistance (Cry1Ac); WO 2005/103266 | Gossypium hirsutum L. (cotton) |
| A-76 | GBH614 | Bayer CropScience (Aventis CropScience (AgrEvo)) | Glyphosate herbicide-tolerant cotton produced by inserting the 2MEPSPS gene into variety Coker312 by Agrobacterium under the control of Ph4a748At and TpotpC. | Gossypium hirsutum L. (cotton) |
| A-77 | LLCotton25 | Bayer CropScience (Aventis CropScience (AgrEvo)) | Glufosinate ammonium herbicide-tolerant cotton produced by inserting a modified phosphinothricin acetyltransferase (PAT)-encoding gene from the soil bacterium Streptomyces hygroscopicus; WO 2003013224 | Gossypium hirsutum L. (cotton) |
| A-78 | LLCotton25 × MON15985 | Bayer CropScience (Aventis CropScience (AgrEvo)) | Stacked herbicide-tolerant and insect-resistant cotton combining tolerance to glufosinate ammonium herbicide from LLCotton25 (OECD identifier: ACS-GHØØ1-3) with resistance to insects from MON15985 (OECD identifier: MON-15985-7). | Gossypium hirsutum L. (cotton) |
| A-79 | MON 15985 | | Insect resistance (Cry1A/Cry2Ab); US 2004-250317 | Gossypium hirsutum L. (cotton) |
| A-80 | MON1445/1698 | Monsanto Company | Glyphosate herbicide-tolerant cotton produced by inserting a naturally glyphosate-tolerant form of the enzyme 5-enolpyruvylshikimate-3-phosphate synthase (EPSPS) from the CP4 strain of A. tumefaciens. | Gossypium hirsutum L. (cotton) |

| No. | Transgenic event | Company | Description | Crop |
|---|---|---|---|---|
| A-81 | MON15985 × MON88913 | Monsanto Company | Stacked insect-resistant and glyphosate-tolerant cotton produced by conventional cross-breeding of the parental lines MON88913 (OECD identifier: MON-88913-8) and 15985 (OECD identifier: MON-15985-7). Glyphosate tolerance is derived from line MON88913 which contains two genes encoding the enzyme 5-enolypyruvylshikimate-3-phosphate synthase (EPSPS) from the CP4 strain of Agrobacterium tumefaciens. Insect resistance is derived from the line MON15985 which was produced by transformation of the DP50B parent variety, which contained event 531 (expressing the Cry1Ac protein), with purified plasmid DNA containing the cry2Ab gene from B. thuringiensis subsp. kurstaki. | Gossypium hirsutum L. (cotton) |
| A-82 | MON-15985-7 × MON-Ø1445-2 | Monsanto Company | Stacked insect-resistant and herbicide-tolerant cotton derived from conventional cross-breeding of the parental lines 15985 (OECD identifier: MON-15985-7) and MON-1445 (OECD identifier: MON-Ø1445-2). | Gossypium hirsutum L. (cotton) |
| A-83 | MON531/757/1076 | Monsanto Company | Insect-resistant cotton produced by inserting the cry1Ac gene from Bacillus thuringiensis subsp. kurstaki HD-73 (B.t.k.). | Gossypium hirsutum L. (cotton) |
| A-84 | MON88913 | Monsanto Company | Glyphosate herbicide-tolerant cotton produced by inserting two genes encoding the enzyme 5-enolypyruvylshikimate-3-phosphate synthase (EPSPS) from the CP4 strain of Agrobacterium tumefaciens; WO 2004/072235 | Gossypium hirsutum L. (cotton) |
| A-85 | MON-ØØ531-6 × MON-Ø1445-2 | Monsanto Company | Stacked insect-resistant and herbicide-tolerant cotton derived from conventional cross-breeding of the parental lines MON531 (OECD identifier: MON-ØØ531-6) and MON-1445 (OECD identifier: MON-Ø1445-2). | Gossypium hirsutum L. (cotton) |
| A-86 | PV-GHGT07 (1445) | | Glyphosate tolerance; US 2004-148666 | Gossypium hirsutum L. (cotton) |
| A-87 | T304-40 | | Insect resistance (Cry1Ab); WO2008/122406 | Gossypium hirsutum L. (cotton) |
| A-88 | T342-142 | | Insect resistance (Cry1Ab); WO 2006/128568 | Gossypium hirsutum L. (cotton) |
| A-89 | X81359 | BASF Inc. | Tolerance to imidazolinone herbicides by selection of a naturally occurring mutant. | Helianthus annuus (sunflower) |
| A-90 | RH44 | BASF Inc. | Selection for a mutagenized version of the enzyme acetohydroxy acid synthase (AHAS), also known as acetolactate synthase (ALS) or acetolactate pyruvate lyase. | Lens culinaris (lentil) |
| A-91 | FP967 | University of Saskatchewan, Crop Dev. Centre | A variant form of acetolactate synthase (ALS) was obtained from a chlorosulfuron-tolerant line of A. thaliana and used to transform flax. | Linum usitatissimum L. (flax, linseed) |
| A-92 | 5345 | Monsanto Company | Resistance to lepidopteran pests through the introduction of the cry1Ac gene from Bacillus thuringiensis subsp. kurstaki. | Lycopersicon esculentum (tomato) |
| A-93 | 8338 | Monsanto Company | Introduction of a gene sequence encoding the enzyme 1-aminocyclopropane-1-carboxylic acid deaminase (ACCd) that metabolizes the precursor of the fruit ripening hormone ethylene. | Lycopersicon esculentum (tomato) |
| A-94 | 1345-4 | DNA Plant Technology Corporation | Delayed ripening tomatoes produced by inserting an additional copy of a truncated gene encoding 1-aminocyclopropane-1-carboxylic acid (ACC) synthase, which resulted in downregulation of the endogenous ACC synthase and reduced ethylene accumulation. | Lycopersicon esculentum (tomato) |
| A-95 | 35 1 N | Agritope Inc. | Introduction of a gene sequence encoding the enzyme S-adenosylmethionine hydrolase that metabolizes the precursor of the fruit ripening hormone ethylene. | Lycopersicon esculentum (tomato) |
| A-96 | B, Da, F | Zeneca Seeds | Delayed softening tomatoes produced by inserting a truncated version of the polygalacturonase (PG)-encoding gene in the sense or anti-sense orientation in order to reduce expression of the endogenous PG gene, and thus reduce pectin degradation. | Lycopersicon esculentum (tomato) |

| No. | Transgenic event | Company | Description | Crop |
|---|---|---|---|---|
| A-97 | FLAVR SAVR | Calgene Inc. | Delayed softening tomatoes produced by inserting an additional copy of the polygalacturonase (PG)-encoding gene in the anti-sense orientation in order to reduce expression of the endogenous PG gene and thus reduce pectin degradation. | *Lycopersicon esculentum* (tomato) |
| A-98 | J101, J163 | Monsanto Company und Forage Genetics International | Glyphosate herbicide-tolerant alfalfa (Lucerne) produced by inserting a gene encoding the enzyme 5-enolypyruvylshikimate-3-phosphate synthase (EPSPS) from the CP4 strain of *Agrobacterium tumefaciens*. | *Medicago sativa* (alfalfa) |
| A-99 | C/F/93/08-02 | Societe National d'Exploitation des Tabacs et Allumettes | Tolerance to the herbicides bromoxynil and ioxynil by incorporation of the nitrilase gene from *Klebsiella pneumoniae*. | *Nicotiana tabacum* L. (tobacco) |
| A-100 | Vector 21-41 | Vector Tobacco Inc. | Reduced nicotine content through introduction of a second copy of the tobacco quinolinic acid phosphoribosyltransferase (QTPase) in the antisense orientation. The NPTII-encoding gene from *E. coli* was introduced as a selectable marker to identify transformants. | *Nicotiana tabacum* L. (tobacco) |
| A-101 | CL121, CL141, CFX51 | BASF Inc. | Tolerance to the imidazolinone herbicide imazethapyr, induced by chemical mutagenesis of the acetolactate synthase (ALS) enzyme using ethyl methanesulfonate (EMS). | *Oryza sativa* (rice) |
| A-102 | GAT-OS2 | | Glufosinate tolerance; WO 01/83818 | *Oryza sativa* (rice) |
| A-103 | GAT-OS3 | | Glufosinate tolerance; US 2008-289060 | *Oryza sativa* (rice) |
| A-104 | IMINTA-1, IMINTA-4 | BASF Inc. | Tolerance to imidazolinone herbicides induced by chemical mutagenesis of the acetolactate synthase (ALS) enzyme using sodium azide. | *Oryza sativa* (rice) |
| A-105 | LLRICE06, LLRICE62 | Aventis CropScience | Glufosinate ammonium herbicide-tolerant rice produced by inserting a modified phosphinothricin acetyltransferase (PAT)-encoding gene from the soil bacterium *Streptomyces hygroscopicus*. | *Oryza sativa* (rice) |
| A-106 | LLRICE601 | Bayer CropScience (Aventis CropScience (AgrEvo)) | Glufosinate ammonium herbicide-tolerant rice produced by inserting a modified phosphinothricin acetyltransferase (PAT)-encoding gene from the soil bacterium *Streptomyces hygroscopicus*. | *Oryza sativa* (rice) |
| A-107 | PE-7 | | Insect resistance (Cry1Ac); WO 2008/114282 | *Oryza sativa* (rice) |
| A-108 | PWC16 | BASF Inc. | Tolerance to the imidazolinon herbicide imazethapyr, induced by chemical mutagenesis of the acetolactate synthase (ALS) enzyme using ethyl methanesulfonate (EMS). | *Oryza sativa* (rice) |
| A-109 | TT51 | | Insect resistance (Cry1Ab/Cry1Ac); CN1840655 | *Oryza sativa* (rice) |
| A-110 | C5 | United States Department of Agriculture-Agricultural Research Service | Plum pox virus (PPV)-resistant plum tree produced through *Agrobacterium*-mediated transformation with a coat protein (CP) gene from the virus. | *Prunus domestica* (plum) |
| | EH92-527 | BASF Plant Science | Crop composition; Amflora; Unique EU identifier: BPS-25271-9 | |
| A-111 | ATBT04-6, ATBT04-27, ATBT04-30, ATBT04-31, ATBT04-36, SPBT02-5, SPBT02-7 | Monsanto Company | Colorado potato beetle-resistant potatoes produced by inserting the cry3A gene from *Bacillus thuringiensis* (subsp. tenebrionis). | *Solanum tuberosum* L. (potato) |
| A-112 | BT6, BT10, BT12, BT16, BT17, BT18, BT23 | Monsanto Company | Colorado potato beetle-resistant potatoes produced by inserting the cry3A gene from *Bacillus thuringiensis* (subsp. tenebrionis). | *Solanum tuberosum* L. (potato) |
| A-113 | RBMT15-101, SEMT15-02, SEMT15-15 | Monsanto Company | Colorado potato beetle- and potato Y-virus (PVY)-resistant potatoes produced by inserting the cry3A gene from *Bacillus thuringiensis* (subsp. tenebrionis) and the (potato) coat protein-encoding gene from PVY. | *Solanum tuberosum* L. |
| A-114 | RBMT21-129, RBMT21-350, RBMT22-082 | Monsanto Company | Colorado potato beetle- and potato leaf roll virus (PLRV)-resistant potatoes produced by inserting the cry3A gene from *Bacillus thuringiensis* (subsp. tenebrionis) and the replicase-encoding gene from PLRV. | *Solanum tuberosum* L. (potato) |

| No. | Transgenic event | Company | Description | Crop |
|---|---|---|---|---|
| A-115 | AP205CL | BASF Inc. | Selection for a mutagenized version of the enzyme acetohydroxy acid synthase (AHAS), also known as acetolactate synthase (ALS) or acetolactate pyruvate lyase. | *Triticum aestivum* (wheat) |
| A-116 | AP602CL | BASF Inc. | Selection for a mutagenized version of the enzyme acetohydroxy acid synthase (AHAS), also known as acetolactate synthase (ALS) or acetolactate pyruvate lyase. | *Triticum aestivum* (wheat) |
| A-117 | BW255-2, BW238-3 | BASF Inc. | Selection for a mutagenized version of the enzyme acetohydroxy acid synthase (AHAS), also known as acetolactate synthase (ALS) or acetolactate pyruvate lyase. | *Triticum aestivum* (wheat) |
| A-118 | BW7 | BASF Inc. | Tolerance to imidazolinone herbicides induced by chemical mutagenesis of the acetohydroxy acid synthase (AHAS) gene using sodium azide. | *Triticum aestivum* (wheat) |
| A-119 | Event 1 | | Fusarium resistance (trichothecene 3-0-cetyltransferase); CA 2561992 | *Triticum aestivum* (wheat) |
| A-120 | JOPLIN1 | | Disease (fungal) resistance (trichothecene 3-O-acetyltransferase); US 2008064032 | Triticum aestivum (wheat) |
| A-121 | MON71800 | Monsanto Company | Glyphosate-tolerant wheat variety produced by inserting a modified 5-enolpyruvylshikimate-3-phosphate synthase (EPSPS)-encoding gene from the CP4 strain of the soil bacterium *Agrobacterium tumefaciens*. | *Triticum aestivum* (wheat) |
| A-122 | SWP965001 | Cyanamid Crop Protection | Selection for a mutagenized version of the enzyme acetohydroxy acid synthase (AHAS), also known as acetolactate synthase (ALS) or acetolactate pyruvate lyase. | *Triticum aestivum* (wheat) |
| A-123 | Teal 11A | BASF Inc. | Selection for a mutagenized version of the enzyme acetohydroxy acid synthase (AHAS), also known as acetolactate synthase (ALS) or acetolactate pyruvate lyase. | *Triticum aestivum* (wheat) |
| A-124 | 176 | Syngenta Seeds, Inc. | Insect-resistant maize produced by inserting the cry1Ab gene from *Bacillus thuringiensis* subsp. kurstaki. The genetic modification affords resistance to attack by the European Corn Borer (ECB). | *Zea mays* L. (maize) |
| A-125 | 3272 | | Self-processing corn (alpha-amylase); US 2006-230473 | *Zea mays* L. (maize) |
| A-126 | 3751IR | Pioneer Hi-Bred International Inc. | Selection of somaclonal variants by culture of embryos on imidazolinone-containing media. | *Zea mays* L. (maize) |
| A-127 | 676, 678, 680 | Pioneer Hi-Bred International Inc. | Male-sterile and glufosinate ammonium herbicide-tolerant maize produced by inserting genes encoding DNA adenine methylase and phosphinothricin acetyltransferase (PAT) from *Escherichia coli* and *Streptomyces viridochromogenes*. | *Zea mays* L. (maize) |
| A-128 | ACS-ZMØØ3-2 × MON-ØØ81Ø-6 | Bayer Crop-Science (Aventis CropScience (AgrEvo)) | Stacked insect-resistant and herbicide-tolerant maize hybrid derived from conventional cross-breeding of the parental lines T25 (OECD identifier: ACS-ZMØØ3-2) and MON810 (OECD identifier: MON-ØØ81Ø-6). | *Zea mays* L. (maize) |
| A-129 | B16 | | Glufosinate resistance; US 2003-126634 | *Zea mays* L. (maize) |
| A-130 | B16 (DLL25) | Dekalb Genetics Corporation | Glufosinate ammonium herbicide-tolerant maize produced by inserting the gene encoding phosphinothricin acetyltransferase (PAT) from *Streptomyces hygroscopicus*. | *Zea mays* L. (maize) |
| A-131 | BT11 (X4334CBR, X4734CBR) | Syngenta Seeds, Inc. | Insect-resistant and herbicide-tolerant maize produced by inserting the cry1Ab gene from *Bacillus thuringiensis* subsp. kurstaki, and the phosphinothricin N-acetyltransferase (PAT)-encoding gene from *S. viridochromogenes*. | *Zea mays* L. (maize) |
| A-132 | BT11 × MIR604 | Syngenta Seeds, Inc. | Stacked insect-resistant and herbicide-tolerant maize produced by conventional cross-breeding of parental lines BT11 (OECD unique identifier: SYN-BTØ11-1) and MIR604 (OECD unique identifier: SYN-IR6Ø5-5). Resistance to the European Corn Borer and tolerance to the herbicide glufosinate ammonium (Liberty) is derived from BT11, which contains the cry1Ab gene from *Bacillus thuringiensis* subsp. kurstaki, and the phosphinothricin N-acetyltransferase (PAT)-encoding gene from *S. viridochromogenes*. Corn rootworm-resistance is derived from MIR604 which contains the mcry3A-gene from *Bacillus thuringiensis*. | *Zea mays* L. (maize) |

-continued

| No. | Transgenic event | Company | Description | Crop |
|---|---|---|---|---|
| A-133 | BT11 × MIR604 × GA21 | Syngenta Seeds, Inc. | Stacked insect-resistant and herbicide-tolerant maize produced by conventional cross-breeding of parental lines BT11 (OECD unique identifier: SYN-BTØ11-1), MIR604 (OECD unique identifier: SYN-IR6Ø5-5) and GA21 (OECD unique identifier: MON- Ø Ø Ø21-9). Resistance to the European Corn Borer and tolerance to the herbicide glufosinate ammonium (Liberty) is derived from BT11, which contains the cry1Ab gene from *Bacillus thuringiensis* subsp. kurstaki, and the phosphinothricin N-acetyltransferase (PAT)-encoding gene from *S. viridochromogenes*. Corn rootworm-resistance is derived from MIR604 which contains the mcry3A gene from *Bacillus thuringiensis*. Tolerance to glyphosate herbicide is derived from GA21 which contains a modified EPSPS gene from maize. | *Zea mays* L. (maize) |
| A-134 | CBH-351 | Aventis CropScience | Insect-resistant and glufosinate ammonium herbicide-tolerant maize developed by inserting the genes encoding Cry9C protein from *Bacillus thuringiensis* subsp. tolworthi and phosphinothricin acetyltransferase (PAT) from *Streptomyces hygroscopicus*. | *Zea mays* L. (maize) |
| A-135 | DAS-06275-8 | DOW AgroSciences LLC | Lepidopteran insect-resistant and glufosinate ammonium herbicide-tolerant maize variety produced by inserting the cry1F gene from *Bacillus thuringiensis* var. aizawai and the phosphinothricin acetyltransferase (PAT) from *Streptomyces hygroscopicus*. | *Zea mays* L. (maize) |
| A-136 | DAS-59122-7 | DOW AgroSciences LLC and Pioneer Hi-Bred International Inc. | Corn rootworm-resistant maize produced by inserting the cry34Ab1 and cry35Ab1 genes from the PS149B1 strain of *Bacillus thuringiensis*. The PAT-encoding gene from *Streptomyces viridochromogenes* was introduced as a selectable marker; US 2006-070139 | *Zea mays* L. (maize) |
| A-137 | DAS-59122-7 × NK603 | DOW AgroSciences LLC and Pioneer Hi-Bred International Inc. | Stacked insect-resistant and herbicide-tolerant maize produced by conventional cross-breeding of parental lines DAS-59122-7 (OECD unique identifier: DAS-59122-7) with NK603 (OECD unique identifier: MON-ØØ6Ø3-6). Corn rootworm-resistance is derived from line DAS-59122-7 which contains the cry34Ab1 and cry35Ab1 genes from the PS149B1 strain of *Bacillus thuringiensis*. Tolerance to glyphosate herbicide is derived from NK603. | *Zea mays* L. (maize) |
| A-138 | DAS-59122-7 × TC1507 × NK603 | DOW AgroSciences LLC and Pioneer Hi-Bred International Inc. | Stacked insect-resistant and herbicide-tolerant maize produced by conventional cross-breeding of parental lines DAS-59122-7 (OECD unique identifier: DAS-59122-7) and TC1507 (OECD unique identifier DAS-Ø15Ø7-1) with NK603 (OECD unique identifier: MON-ØØ6Ø3-6). Corn rootworm-resistance is derived from line DAS-59122-7, which contains the cry34Ab1 and cry35Ab1 genes from the PS149B1 strain of *Bacillus thuringiensis*. Lepidopteran resistance and tolerance to glufosinate ammonium herbicide are derived from TC1507. Tolerance to glyphosate herbicide is derived from NK603. | *Zea mays* L. (maize) |
| A-139 | DAS-Ø15Ø7-1 × MON-ØØ6Ø3-6 | DOW AgroSciences LLC | Stacked insect-resistant and herbicide-tolerant maize derived from conventional cross-breeding of the parental lines 1507 (OECD identifier: DAS-Ø15Ø7-1) and NK603 (OECD identifier: MON-ØØ6Ø3-6). | *Zea mays* L. (maize) |
| A-140 | DBT418 | Dekalb Genetics Corporation | Insect-resistant and glufosinate ammonium herbicide-tolerant maize developed by inserting genes encoding Cry1AC protein from *Bacillus thuringiensis* subsp kurstaki and phosphinothricin acetyltransferase (PAT) from *Streptomyces hygroscopicus*. | *Zea mays* L. (maize) |
| A-141 | DK404SR | BASF Inc. | Somaclonal variants with a modified acetyl-CoA-carboxylase (ACCase) were selected by culture of embryos on sethoxydim-enriched medium. | *Zea mays* L. (maize) |
| A-142 | DP-098140-6 | | Glyphosate tolerance/ALS inhibitor tolerance; WO 2008/112019 | *Zea mays* L. (maize) |
| A-143 | DP-Ø9814Ø-6 (Event 98140) | Pioneer Hi-Bred International Inc. | Maize line 98140 was genetically engineered to express the GAT4621 (glyphosate acetyltransferase) and ZM-HRA (modified maize version of a acetolactate synthase) proteins. The GAT4621 protein, encoded by the gat4621 gene, confers tolerance to glyphosate-containing herbicides by acetylating glyphosate and thereby rendering it non-phytotoxic. The ZM-HRA protein, encoded by the zm-hra gene, confers tolerance to the ALS-inhibiting class of herbicides. | *Zea mays* L. (maize) |

| No. | Transgenic event | Company | Description | Crop |
|---|---|---|---|---|
| A-144 | Event 3272 | Syngenta Seeds, Inc. | Maize line expressing a heat-stable alpha-amylase gene amy797E for use in the dry-grind ethanol production process. The phosphomannose isomerase gene from *E. coli* was used as a selectable marker. | *Zea mays* L. (maize) |
| A-145 | EXP1910IT | Syngenta Seeds, Inc. (formerly Zeneca Seeds) | Tolerance to the imidazolinone herbicide imazethapyr, induced by chemical mutagenesis of the acetolactate synthase (ALS) enzyme using ethyl methanesulfonate (EMS). | *Zea mays* L. (maize) |
| A-146 | FI117 | | Glyphosate resistance; US 6,040,497 | *Zea mays* L. (maize) |
| A-147 | GA21 | Monsanto Company | Induction, by gene-gun bombardment, of a modified 5-enolpyruvylshikimate-3-phosphate synthase (EPSPS), an enzyme involved in the shikimate biosynthesis pathway for the production of the aromatic amino acids. | *Zea mays* L. (maize) |
| A-148 | GAT-ZM1 | | Glufosinate tolerance; WO 01/51654 | *Zea mays* L. (maize) |
| A-149 | GG25 | | Glyphosate resistance; US 6,040,497 | *Zea mays* L. (maize) |
| A-150 | GJ11 | | Glyphosate resistance; US 6,040,497 | *Zea mays* L. (maize) |
| A-151 | IT | Pioneer Hi-Bred International Inc. | Tolerance to the imidazolinone herbicide imazethapyr, was obtained by in vitro selection of somaclonal variants. | *Zea mays* L. (maize) |
| A-152 | LY038 | Monsanto Company | Altered amino acid composition, specifically elevated levels of lysine, through the introduction of the cordapA gene, derived from Corynebacterium glutamicum, encoding the enzyme dihydrodipicolinate synthase (cDHDPS); US 7,157,281 | *Zea mays* L. (maize) |
| A-153 | MIR162 | | Insect resistance; WO 2007142840 | *Zea mays* L. (maize) |
| A-154 | MIR604 | Syngenta Seeds, Inc. | Corn rootworm-resistant maize was produced by transformation with a modified cry3A gene. The phosphomannose isomerase gene from *E. coli* was used as a selectable marker; (Cry3a055); EP 1 737 290 | *Zea mays* L. (maize) |
| A-155 | MIR604 x GA21 | Syngenta Seeds, Inc. | Stacked insect-resistant and herbicide-tolerant maize produced by conventional cross-breeding of parental lines MIR604 (OECD unique identifier: SYN-IR6Ø5-5) and GA21 (OECD unique identifier: MON-ØØØ21-9). Corn rootworm-resistance is derived from MIR604 which contains the mcry3A gene from *Bacillus thuringiensis*. Tolerance to glyphosate herbicide is derived from GA21. | *Zea mays* L. (maize) |
| A-156 | MON80100 | Monsanto Company | Insect-resistant maize produced by inserting the cry1Ab gene from *Bacillus thuringiensis* subsp. kurstaki. The genetic modification affords resistance to attack by the European Corn Borer. | *Zea mays* L. (maize) |
| A-157 | MON802 | Monsanto Company | Insect-resistant and glyphosate herbicide-tolerant maize produced by inserting the genes encoding the Cry1Ab protein from *Bacillus thuringiensis* and the 5-enolpyruvylshikimate-3-posphate synthase (EPSPS) from the CP4 strain of *A. tumefaciens*. | *Zea mays* L. (maize) |
| A-158 | MON809 | Pioneer Hi-Bred International Inc. | Resistance to European Corn Borer (*Ostrinia nubilalis*) by introduction of a synthetic cry1Ab gene. Glyphosate resistance via introduction of the bacterial version of a plant enzyme, 5-enolpyruvylshikimat-3-phosphate synthase (EPSPS). | *Zea mays* L. (maize) |
| A-159 | MON810 | Monsanto Company | Insect-resistant maize produced by inserting a truncated form of the cry1Ab gene from *Bacillus thuringiensis* subsp. kurstaki HD-1. The genetic modification affords resistance to attack by the European Corn Borer (ECB); US 2004-180373 | *Zea mays* L. (maize) |
| A-160 | MON810 x MON88017 | Monsanto Company | Stacked insect-resistant and glyphosate-tolerant maize derived from conventional cross-breeding of the parental lines MON810 (OECD identifier: MON-ØØ81Ø-6) and MON88017 (OECD identifier: MON-88Ø17-3). European Corn Borer (ECB) resistance is derived from a truncated form of the cry1Ab gene from *Bacillus thuringiensis* subsp. kurstaki HD-1, present in MON810. Corn rootworm-resistance is derived from the cry3Bb1 gene from the EG4691 strain of *Bacillus thuringiensis* subspecies kumamotoensis present in MON88017. Glyphosate tolerance is derived from a 5-enolpyruvylshikimate-3-phosphate synthase (EPSPS)-encoding gene from the CP4 strain of *Agrobacterium tumefaciens* present in MON88017. | *Zea mays* L. (maize) |

-continued

| No. | Transgenic event | Company | Description | Crop |
|---|---|---|---|---|
| A-161 | MON832 | Monsanto Company | Introduction, by gene-gun bombardment, of glyphosate oxidase (GOX) and a modified 5-enolpyruvylshikimate-3-phosphate synthase (EPSPS), an enzyme involved in the shikimate biosynthesis pathway for the production of the aromatic amino acids. | Zea mays L. (maize) |
| A-162 | MON863 | Monsanto Company | Corn rootworm-resistant maize produced by inserting the cry3Bb1 gene from Bacillus thuringiensis subsp. kumamotoensis. | Zea mays L. (maize) |
| A-163 | MON87460 | | Drought tolerance; water deficit tolerance; WO 2009/111263 | Zea mays L. (maize) |
| A-164 | MON88017 | Monsanto Company | Corn rootworm-resistant maize produced by inserting the cry3Bb1 gene from the EG4691 strain of Bacillus thuringiensis subsp. kumamotoensis. Glyphosate tolerance was derived by inserting a 5-enolpyruvylshikimate-3-phosphate synthase (EPSPS)-encoding gene from the CP4 strain of Agrobacterium tumefaciens; WO 2005059103 | Zea mays L. (maize) |
| A-165 | MON89034 | Monsanto Company | Maize event expressing two different insecticidal proteins from Bacillus thuringiensis providing resistance to a number of lepidopteran pests; insect resistance (Lipidoptera-Cry1A.105-Cry2Ab); WO 2007140256 | Zea mays L. (maize) |
| A-166 | MON89034 × MON88017 | Monsanto Company | Stacked insect-resistant and glyphosate-tolerant maize derived from conventional cross-breeding of the parental lines MON89034 (OECD identifier: MON-89 Ø34-3) and MON88017 (OECD identifier: MON-88Ø17-3). Resistance to lepidopteran insects is derived from two cry genes present in MON89043. Corn rootworm-resistance is derived from a single cry gene and glyphosate tolerance is derived from a 5-enolpyruvylshikimate-3-phosphate synthase (EPSPS)-encoding gene from Agrobacterium tumefaciens present in MON88017. | Zea mays L. (maize) |
| A-167 | MON-ØØ6Ø3-6 × MON-ØØ81Ø-6 | Monsanto Company | Stacked insect-resistant and herbicide-tolerant maize hybrid derived from conventional cross-breeding of the parental lines NK603 (OECD identifier: MON-ØØ6Ø3-6) and MON810 (OECD identifier: MON-ØØ81Ø-6). | Zea mays L. (maize) |
| A-168 | MON-ØØ81Ø-6 × LY038 | Monsanto Company | Stacked insect-resistant and increased lysine-content maize hybrid derived from conventional cross-breeding of the parental lines MON810 (OECD identifier: MON-ØØ81Ø-6) and LY038 (OEC identifier: REN-ØØØ38-3). | Zea mays L. (maize) |
| A-169 | MON-ØØ863-5 × MON-ØØ6Ø3-6 | Monsanto Company | Stacked insect-resistant and herbicide-tolerant maize hybrid derived from conventional cross-breeding of the parental lines MON863 (OECD identifier: MON-ØØ863-5) and NK603 (OECD identifier: MON-ØØ6Ø3-6). | Zea mays L. (maize) |
| A-170 | MON-00863-5 × MON-00810-6 | Monsanto Company | Stacked insect-resistant maize hybrid derived from conventional cross-breeding of the parental lines MON863 (OECD identifier: MON-ØØ863-5) and MON810 (OECD identifier: MON-ØØ81Ø-6) | Zea mays L. (maize) |
| A-171 | MON-ØØ863-5 × MON-ØØ81Ø-6 × MON-ØØ6Ø3-6 | Monsanto Company | Stacked insect-resistant and herbicide-tolerant maize hybrid derived from conventional cross-breeding of the stacked hybrids MON-ØØ863-5 × MON-ØØ81Ø-6 and NK603 (OECD identifier: MON-ØØ6Ø3-6). | Zea mays L. (maize) |
| A-172 | MON-ØØØ21-9 × MON-ØØ81Ø-6 | Monsanto Company | Stacked insect-resistant and herbicide-tolerant maize hybrid derived from conventional cross-breeding of the parental lines GA21 (OECD identifier: MON-ØØØ21-9) and MON810 (OECD identifier: MON-ØØ81Ø-6). | Zea mays L. (maize) |
| A-173 | MS3 | Bayer CropScience (Aventis CropScience (AgrEvo)) | Male sterility caused by expression of the barnase ribonuclease gene from Bacillus amyloliquefaciens; PPT resistance was obtained via PPT acetyltransferase (PAT). | Zea mays L. (maize) |
| A-174 | MS6 | Bayer CropScience (Aventis CropScience (AgrEvo)) | Male sterility caused by expression of the barnase ribonuclease gene from Bacillus amyloliquefaciens; PPT resistance was attained via PPT acetyltransferase (PAT). | Zea mays L. (maize) |
| A-175 | NK603 | Monsanto Company | Introduction by gene-gun bombardment of a modified 5-enolpyruvylshikimate-3-phosphate synthase (EPSPS), an enzyme involved in the shikimate biosynthesis pathway for the production of the aromatic amino acids. | Zea mays L. (maize) |
| A-176 | PV-ZMGT32 (NK603) | | Glyphosate tolerance; US 2007-056056 | Zea mays L. (maize) |

-continued

| No. | Transgenic event | Company | Description | Crop |
|---|---|---|---|---|
| A-177 | PV-ZMGT32(nk603) | | Glyphosate tolerance; US 2007292854 | *Zea mays* L. (maize) |
| A-178 | PV-ZMIR13 (MON863) | | Insect resistance (Cry3Bb); US 2006-095986 | *Zea mays* L. (maize) |
| A-179 | SYN-BTØ11-1 × MON-ØØØ21-9 | Syngenta Seeds, Inc. | Stacked insect-resistant and herbicide-tolerant maize produced by conventional cross-breeding of parental lines BT11 (OECD unique identifier: SYN-BTØ11-1) and GA21 (OECD unique identifier: MON-ØØØ21-9). | *Zea mays* L. (maize) |
| A-180 | T14, T25 | Bayer CropScience (Aventis CropScience (AgrEvo)) | Glufosinate herbicide-tolerant maize produced by inserting the phosphinothricin N-acetyltranferase (PAT)-encoding gene from the aerobic actinomycete *Streptomyces viridochromogenes*. | *Zea mays* L. (maize) |
| A-181 | TC1507 | Mycogen (c/o Dow AgroSciences); Pioneer (c/o Dupont) | Insect-resistant and glufosinate ammonium herbicide-tolerant maize produced by inserting the cry1F gene from *Bacillus thuringiensis* var. aizawai and the phosphinothricin N-acetyltransferase-encoding gene from *Streptomyces viridochromogenes*. | *Zea mays* L. (maize) |
| A-182 | TC1507 × DAS-59122-7 | DOW AgroSciences LLC and Pioneer Hi-Bred International Inc. | Stacked insect-resistant and herbicide-tolerant maize produced by conventional cross-breeding of parental lines TC1507 (OECD unique identifier: DAS-Ø15Ø7-1) with DAS-59122-7 (OECD unique identifier: DAS-59122-7). Resistance to lepidopteran insects is derived from TC1507 due to the presence of the cry1F gene from *Bacillus thuringiensis* var. aizawai. Corn rootworm-resistance is derived from line DAS-59122-7 which contains the cry34Ab1 and cry35Ab1 genes from *Bacillus*. *Thuringiensis* strain PS149B1. Tolerance to glufosinate ammonium herbicide is derived from TC1507 from the phosphinothricin N-acetyltransferase-encoding gene from *Streptomyces viridochromogenes*. | *Zea mays* L. (maize) |
| A-183 | VIP1034 | | Insect resistance; WO 03/052073 | *Zea mays* L. (maize) |

In one embodiment of the invention the plants B-1 to B-129 of table B, in total or in part, or propagation material of said plants, is treated or contacted with the active ingredient combinations of the invention, alone or in the form of compositions comprising an active ingredient combination.

TABLE B

Non-exhaustive list of transgenic plants to carry out the invention from the APHIS database of the United States Department of Agriculture (USDA). The database can be found on: http://www.aphis.usda.gov/animal_welfare/efoia/index.shtml.

| No. | Petition | Extension of Petition*** | Institution | Plant | Transformation Event or Line | EA final conclusion & determination |
|---|---|---|---|---|---|---|
| B-1 | 10-070-01p | | Virginia Tech | Peanut | Sclerotinia blight-resistant | N70, P39 and W171 |
| B-2 | 09-349-01p | | Dow AgroSciences | Soya bean | 2,4-D- and glufosinate tolerance | DAS-68416-4 |
| B-3 | 09-328-01p | | Bayer Crop Science | Soya bean | glyphosate and isoxaflutole tolerance | FG72 |
| B-4 | 09-233-01p | | Dow | Maize | 2,4-D and ACCase-inhibitor tolerance | DAS-40278-9 |
| B-5 | 09-201-01p | | Monsanto | Soya bean | improved fatty acid profile | MON-877Ø5-6 |
| B-6 | 09-183-01p | | Monsanto | Soya bean | stearidonic acid production | MON-87769 |
| B-7 | 09-082-01p | | Monsanto | Soya bean | Lepidopteran resistance | MON 87701 |
| B-8 | 09-063-01p | | Stine Seed | Maize | Glyphosate tolerance | HCEM485 |
| B-9 | 09-055-01p | | Monsanto | Maize | Drought tolerance | MON 87460 |
| B-10 | 09-015-01p | | BASF Plant Science, LLC | Soya bean | Imidazolinon tolerance | BPS-CV127-9 Soya bean |
| B-11 | 08-366-01p | | ArborGen | *Eucalyptus* | Freeze tolerance, fertility altered | ARB-FTE1-08 |

TABLE B-continued

Non-exhaustive list of transgenic plants to carry out the invention from the APHIS database of the United States Department of Agriculture (USDA). The database can be found on: http://www.aphis.usda.gov/animal_welfare/efoia/index.shtml.

| No. | Petition | Extension of Petition*** | Institution | Plant | Transformation Event or Line | EA final conclusion & determination |
|---|---|---|---|---|---|---|
| B-12 | 08-340-01p | | Bayer | Cotton | Glufosinate tolerance, insect resistance | T304-40XGHB119 |
| B-13 | 08-338-01p | | Pioneer | Maize | Male sterility, fertility restored, visual marker | DP-32138-1 |
| B-14 | 08-315-01p | | Florigene | Rose | Altered flower color | IFD-52Ø1-4 and IFD-529Ø1-9 |
| B-15 | 07-108-01p | | Syngenta | Cotton | Lepidopteran resistance | COT67B |
| B-16 B-17 | 06-354-01p | | Pioneer | Soya bean | High oleic acid content | DP-3Ø5423-1 |
| B-18 B-19 | 05-280-01p | | Syngenta | Maize | Thermostable alpha-amylase | 3272 |
| B-20 B-21 B-22 B-23 | 04-110-01p | | Monsanto & Forage Genetics | Alfalfa | Glyphosate tolerance | J101, J163 |
| B-24 B-25 B-26 B-27 B-28 B-29 | 03-104-01p | | Monsanto & Scotts | Creeping bentgrass | Glyphosate tolerance | ASR368 |
| B-30 B-31 | 07-253-01p | | Syngenta | Maize | Lepidopteran resistance | MIR-162 Maize |
| B-32 B-33 | 07-152-01p | | Pioneer | Maize | Glyphosate & imidazolinone tolerance | DP-098140-6 |
| B-34 B-35 | 04-337-01p | | University of Florida | *Papaya* | *Papaya* ringspot virus-resistant | X17-2 |
| B-36 B-37 | 06-332-01p | | Bayer Crop Science | Cotton | Glyphosate tolerance | GHB614 |
| B-38 B-39 | 06-298-01p | | Monsanto | Maize | European Corn Borer resistance | MON 89034 |
| B-40 B-41 | 06-271-01p | | Pioneer | Soya bean | Glyphosate & acetolactate synthase tolerance | 356043 (DP-356Ø43-5) |
| B-42 B-43 | 06-234-01p | 98-329-01p | Bayer Crop Science | Rice | Phosphinothricin tolerance | LLRICE601 |
| B-44 B-45 | 06-178-01p | | Monsanto | Soya bean | Glyphosate tolerance | MON 89788 |
| B-46 B-47 B-48 | 04-362-01p | | Syngenta | Maize | Corn rootworm-protected | MIR604 |
| B-49 B-50 | 04-264-01p | | ARS | Plum | Plum Pox virus-resistant | C5 |
| B-51 B-52 | 04-229-01p | | Monsanto | Maize | High lysine content | LY038 |
| B-53 B-54 | 04-125-01p | | Monsanto | Maize | Corn rootworm-resistance | 88017 |
| B-55 B-56 B-57 | 04-086-01p | | Monsanto | Cotton | Glyphosate tolerance | MON 88913 |
| B-58 B-59 | 03-353-01p | | Dow | Maize | Corn rootworm-resistance | 59122 |
| B-60 B-61 | 03-323-01p | | Monsanto | Sugar beet | Glyphosate tolerance | H7-1 |
| B-62 B-63 | 03-181-01p | 00-136-01p | Dow | Maize | Lepidopteran resistance & phosphinothricin tolerance | TC-6275 |
| B-64 B-65 | 03-155-01p | | Syngenta | Cotton | Lepidopteran resistance | COT 102 |
| B-66 B-67 | 03-036-01p | | Mycogen/Dow | Cotton | Lepidopteran resistance | 281-24-236 |
| B-68 B-69 | 03-036-02p | | Mycogen/Dow | Cotton | Lepidopteran resistance | 3006-210-23 |
| B-70 | 02-042-01p | | Aventis | Cotton | Phosphinothricin tolerance | LLCotton25 |
| B-71 | 01-324-01p | 98-216-01p | Monsanto | Oilseed rape | Glyphosate tolerance | RT200 |

TABLE B-continued

Non-exhaustive list of transgenic plants to carry out the invention from the APHIS database of the United States Department of Agriculture (USDA). The database can be found on: http://www.aphis.usda.gov/animal_welfare/efoia/index.shtml.

| No. | Petition | Extension of Petition*** | Institution | Plant | Transformation Event or Line | EA final conclusion & determination |
|---|---|---|---|---|---|---|
| B-72 | 01-206-01p | 98-278-01p | Aventis | Oilseed rape | Phosphinothricin-tolerance & pollination control | MS1 & RF1/RF2 |
| B-73 | 01-206-02p | 97-205-01p | Aventis | Oilseed rape | phosphinothricin tolerance | Topas 19/2 |
| B-74 | 01-137-01p | | Monsanto | Maize | Corn rootworm-resistance | MON 863 |
| B-75 | 01-121-01p | | Vector | Tobacco | Reduced nicotine content | Vector 21-41 |
| B-76 | 00-342-01p | | Monsanto | Cotton | Lepidopteran resistance | Cotton Event 15985 |
| B-77 | 00-136-01p | | Mycogen c/o Dow & Pioneer | Maize | Lepidopteran resistance & phosphinothricin tolerance | Line 1507 |
| B-78 | 00-011-01p | 97-099-01p | Monsanto | Maize | Glyphosate tolerance | NK603 |
| B-79 | 99-173-01p | 97-204-01p | Monsanto | Potato | PLRV & CPB resistance | RBMT22-82 |
| B-80 | 98-349-01p | 95-228-01p | AgrEvo | Maize | Phosphinothricin tolerance and male sterility | MS6 |
| B-81 | 98-335-01p | | U. of Saskatchewan | Flax | Tolerant to soil residues of sulfonylurea herbicide | CDC Triffid |
| B-82 | 98-329-01p | | AgrEvo | Rice | Phosphinothricin tolerance | LLRICE06, LLRICE62 |
| B-83 | 98-278-01p | | AgrEvo | Oilseed rape | Phosphinothricin tolerance & pollination control | MS8 & RF3 |
| B-84 | 98-238-01p | | AgrEvo | Soya bean | phosphinothricin tolerance | GU262 |
| B-85 | 98-216-01p | | Monsanto | Oilseed rape | Glyphosate tolerance | RT73 |
| B-86 | 98-173-01p | | Novartis Seeds & Monsanto | Beet | Glyphosate tolerance | GTSB77 |
| B-87 | 98-014-01p | 96-068-01p | AgrEvo | Soya bean | Phosphinothricin tolerance | A5547-127 |
| B-88 | 97-342-01p | | Pioneer | Maize | Male sterility & phosphinothricin tolerance | 676, 678, 680 |
| B-89 | 97-339-01p | | Monsanto | Potato | CPB & PVY resistance | RBMT15-101, SEMT15-02, SEMT15-15 |
| B-90 | 97-336-01p | | AgrEvo | Beet | phosphinothricin tolerance | T-120-7 |
| B-91 | 97-287-01p | | Monsanto | Tomato | Lepidopteran resistance | 5345 |
| B-92 | 97-265-01p | | AgrEvo | Maize | Phosphinothricin tolerance & Lepidopteran resistance | CBH-351 |
| B-93 | 97-205-01p | | AgrEvo | Oilseed rape | Phosphinothricin tolerance | T45 |
| B-94 | 97-204-01p | | Monsanto | Potato | CPB & PLRV resistance | RBMT21-129 & RBMT21-350 |
| B-95 | 97-148-01p | | Bejo | *Cichorium intybus* | Male sterility | RM3-3, RM3-4, RM3-6 |
| B-96 | 97-099-01p | | Monsanto | Maize | Glyphosate tolerance | GA21 |
| B-97 | 97-013-01p | | Calgene | Cotton | Bromoxynil tolerance & Lepidopteran resistance | Events 31807 & 31808 |
| B-98 | 97-008-01p | | Du Pont | Soya bean | Oil profile altered | G94-1, G94-19, G-168 |
| B-99 | 96-317-01p | | Monsanto | Maize | Glyphosate tolerance & ECB resistance | MON802 |
| B-100 | 96-291-01p | | DeKalb | Maize | European Corn Borer resistance | DBT418 |

TABLE B-continued

Non-exhaustive list of transgenic plants to carry out the invention from the APHIS database of the United States Department of Agriculture (USDA). The database can be found on: http://www.aphis.usda.gov/animal_welfare/efoia/index.shtml.

| No. | Petition | Extension of Petition*** | Institution | Plant | Transformation Event or Line | EA final conclusion & determination |
|---|---|---|---|---|---|---|
| B-101 | 96-248-01p | 92-196-01p | Calgene | Tomato | Fruit ripening altered | 1 additional FLAVRSAVR line |
| B-102 | 96-068-01p | | AgrEvo | Soya bean | Phosphinothricin tolerance | W62, W98, A2704-12, A2704-21, A5547-35 |
| B-103 | 96-051-01p | | Cornell U | *Papaya* | PRSV resistance | 55-1, 63-1 |
| B-104 | 96-017-01p | 95-093-01p | Monsanto | Maize | European Corn Borer resistance | MON809 & MON810 |
| B-105 | 95-352-01p | | Asgrow | Summer squash | CMV, ZYMV, WMV2 resistance | CZW-3 |
| B-106 | 95-338-01p | | Monsanto | Potato | CPB resistance | SBT02-5 & -7, ATBT04-6 &-27, -30, -31, -36 |
| B-107 | 95-324-01p | | Agritope | Tomato | Fruit ripening altered | 35 1 N |
| B-108 | 95-256-01p | | Du Pont | Cotton | Sulfonylurea resistance | 19-51a |
| B-109 | 95-228-01p | | Plant Genetic Systems | Maize | Male sterile | MS3 |
| B-110 | 95-195-01p | | Northrup King | Maize | European Corn Borer resistance | Bt11 |
| B-111 | 95-179-01p | 92-196-01p | Calgene | Tomato | Fruit ripening altered | 2 additional FLAVRSAVR-lines |
| B-112 | 95-145-01p | | DeKalb | Maize | Phosphinothricin tolerance | B16 |
| B-113 | 95-093-01p | | Monsanto | Maize | Lepidopteran resistance | MON 80100 |
| B-114 | 95-053-01p | | Monsanto | Tomato | Fruit ripening altered | 8338 |
| B-115 | 95-045-01p | | Monsanto | Cotton | Glyphosate tolerance | 1445, 1698 |
| B-116 | 95-030-01p | 92-196-01p | Calgene | Tomato | Fruit ripening altered | 20 additional FLAVRSAVR lines |
| B-117 | 94-357-01p | | AgrEvo | Maize | Phosphinothricin tolerance | T14, T25 |
| B-118 | 94-319-01p | | Ciba Seeds | Maize | Lepidopteran resistance | Event 176 |
| B-119 | 94-308-01p | | Monsanto | Cotton | Lepidopteran resistance | 531, 757, 1076 |
| B-120 | 94-290-01p | | Zeneca & Petoseed | Tomato | Fruit polygalacturonase level decreased | B, Da, F |
| B-121 | 94-257-01p | | Monsanto | Potato | Coleopteran resistance | BT6, BT10, BT12, BT16, BT17, BT18, BT23 |
| B-122 | 94-230-01p | 92-196-01p | Calgene | Tomato | Fruit ripening altered | 9 additional FLAVRSAVR lines |
| B-123 | 94-228-01p | | DNA Plant Tech | Tomato | Fruit ripening altered | 1345-4 |
| B-124 | 94-227-01p | 92-196-01p | Calgene | Tomato | Fruit ripening altered | Line N73 1436-111 |
| B-125 | 94-090-01p | | Calgene | Oilseed rape | Oil profile altered | pCGN3828-212/86-18 & 23 |
| B-126 | 93-258-01p | | Monsanto | Soya bean | Glyphosate tolerance | 40-3-2 |
| B-127 | 93-196-01p | | Calgene | Cotton | Bromoxynil tolerance | BXN |
| B-128 | 92-204-01p | | Upjohn | Summer squash | WMV2 & ZYMV resistance | ZW-20 |

TABLE B-continued

Non-exhaustive list of transgenic plants to carry out the invention from the APHIS database of the United States Department of Agriculture (USDA). The database can be found on: http://www.aphis.usda.gov/animal_welfare/efoia/index.shtml.

| No. | Petition | Extension of Petition*** | Institution | Plant | Transformation Event or Line | EA final conclusion & determination |
|---|---|---|---|---|---|---|
| B-129 | 92-196-01p | | Calgene | Tomato | Fruit ripening altered | FLAVR SAVR |

Abbreviations used in this table:
CMV—cucumber mosaic virus,
CPB—Colorado potato beetle,
PLRV—potato leafroll virus,
PRSV—*papaya* ringspot virus,
PVY—potato virus Y,
WMV2—watermelon mosaic virus 2
ZYMV—zucchini yellow mosaic virus In one embodiment the plants which comprise a transgenic event as per D-1 to D-48 of table D or express such a trait, in whole or in part, or propagation material of these plants, are or is contacted or treated with the active ingredient combinations of the invention, alone or in the form of compositions which comprise an active ingredient combination.

TABLE D

Non-exhaustive list of transgenic events and traits the invention can be worked on, with reference to patent applications.

| No. | Plant species | Transgenic event | Trait | Patent reference |
|---|---|---|---|---|
| D-1 | Maize | PV-ZMGT32 (NK603) | Glyphosate tolerance | US 2007-056056 |
| D-2 | Maize | MIR604 | Insect resistance (Cry3a055) | EP-A 1 737 290 |
| D-3 | Maize | LY038 | High lysine content | U.S. Pat. No. 7,157,281 |
| D-4 | Maize | 3272 | Self-processing maize (alpha-amylase) | US 2006-230473 |
| D-5 | Maize | PV-ZMIR13 (MON863) | Insect resistance (Cry3Bb) | US 2006-095986 |
| D-6 | Maize | DAS-59122-7 | Insect resistance (Cry34Ab1/Cry35Ab1) | US 2006-070139 |
| D-7 | Maize | TC1507 | Insect resistance (Cry1F) | U.S. Pat. No. 7,435,807 |
| D-8 | Maize | MON810 | Insect resistance (Cry1Ab) | US 2004-180373 |
| D-9 | Maize | VIP1034 | Insect resistance | WO 03/052073 |
| D-10 | Maize | B16 | Glufosinate resistance | US 2003-126634 |
| D-11 | Maize | GA21 | Glyphosate resistance | U.S. Pat. No. 6,040,497 |
| D-12 | Maize | GG25 | Glyphosate resistance | U.S. Pat. No. 6,040,497 |
| D-13 | Maize | GJ11 | Glyphosate resistance | U.S. Pat. No. 6,040,497 |
| D-14 | Maize | FI117 | Glyphosate resistance | U.S. Pat. No. 6,040,497 |
| D-15 | Maize | GAT-ZM1 | Glufosinate tolerance | WO 01/51654 |
| D-16 | Maize | DP-098140-6 | Glyphosate tolerance/ALS-inhibitor tolerance | WO 2008/112019 |
| D-17 | Wheat | Event 1 | Fusarium resistance (trichothecene 3-O-acetyltransferase) | CA 2561992 |
| D-18 | Sugar beet | T227-1 | Glyphosate tolerance | US 2004-117870 |
| D-19 | Sugar beet | H7-1 | Glyphosate tolerance | WO 2004-074492 |
| D-20 | Soya bean | MON89788 | Glyphosate tolerance | US 2006-282915 |
| D-21 | Soya bean | A2704-12 | Glufosinate tolerance | WO 2006/108674 |
| D-22 | Soya bean | A5547-35 | Glufosinate tolerance | WO 2006/108675 |
| D-23 | Soya bean | DP-305423-1 | High oleic acid/ALS-inhibitor tolerance | WO 2008/054747 |
| D-24 | Rice | GAT-OS2 | Glufosinate tolerance | WO 01/83818 |
| D-25 | Rice | GAT-OS3 | Glufosinate tolerance | US 2008-289060 |
| D-26 | Rice | PE-7 | Insect resistance (Cry1Ac) | WO 2008/114282 |
| D-27 | Oilseed rape | MS-B2 | Male sterility | WO 01/31042 |
| D-28 | Oilseed rape | MS-BN1/RF-BN1 | Male sterility/restoration | WO 01/41558 |
| D-29 | Oilseed rape | RT73 | Glyphosate resistance | WO 02/36831 |
| D-30 | Cotton | CE43-67B | Insect resistance (Cry1Ab) | WO 2006/128573 |
| D-31 | Cotton | CE46-02A | Insect resistance (Cry1Ab) | WO 2006/128572 |
| D-32 | Cotton | CE44-69D | Insect resistance (Cry1Ab) | WO 2006/128571 |
| D-33 | Cotton | 1143-14A | Insect resistance (Cry1Ab) | WO 2006/128569 |
| D-34 | Cotton | 1143-51B | Insect resistance (Cry1Ab) | WO 2006/128570 |
| D-35 | Cotton | T342-142 | Insect resistance (Cry1Ab) | WO 2006/128568 |
| D-36 | Cotton | event3006-210-23 | Insect resistance (Cry1Ac) | WO 2005/103266 |
| D-37 | Cotton | PV-GHGT07 (1445) | Glyphosate tolerance | US 2004-148666 |
| D-38 | Cotton | MON88913 | Glyphosate tolerance | WO 2004/072235 |
| D-39 | Cotton | EE-GH3 | Glyphosate tolerance | WO 2007/017186 |
| D-40 | Cotton | T304-40 | Insect resistance (Cry1Ab) | WO2008/122406 |

TABLE D-continued

Non-exhaustive list of transgenic events and traits the invention can be worked on, with reference to patent applications.

| No. | Plant species | Transgenic event | Trait | Patent reference |
|---|---|---|---|---|
| D-41 | Cotton | Cot202 | Insect resistance (VIP3) | US 2007-067868 |
| D-42 | Cotton | LLcotton25 | Glufosinate resistance | WO 2007/017186 |
| D-43 | Cotton | EE-GH5 | Insect resistance (Cry1Ab) | WO 2008/122406 |
| D-44 | Cotton | event 281-24-236 | Insect resistance (Cry1F) | WO 2005/103266 |
| D-45 | Cotton | Cot102 | Insect resistance (Vip3A) | US 2006-130175 |
| D-46 | Cotton | MON 15985 | Insect resistance (Cry1A/Cry2Ab) | US 2004-250317 |
| D-47 | Bentgrass | Asr-368 | Glyphosate tolerance | US 2006-162007 |
| D-48 | Aubergine | EE-1 | Insect resistance (Cry1Ac) | WO 2007/091277 |

In one embodiment the plants which comprise a transgenic event as per E-1 to E-50 of table E or express such a trait, in whole or in part, or propagation material of these plants, are or is contacted or treated with the active ingredient combinations of the invention, alone or in the form of compositions which comprise an active ingredient combination.

TABLE E

Non-exhaustive list of transgenic events and traits and their trade names.

| No. | Trade name | Plant | Company | Genetically modified properties | Additional information |
|---|---|---|---|---|---|
| E-1 | Roundup Ready ® | *Beta vulgaris* (sugar beet) | Monsanto Company | Glyphosate tolerance | |
| E-2 | InVigor ® | *Brassica napus* (Argentine canola rape) | Bayer CropScience | Canola rape was genetically modified with the following result:<br>Ø expression of a gene which confers tolerance to the herbicide glyfosinate ammonium;<br>Ø introduction of a novel hybrid breeding system for canola rape which is based on genetically modified male-sterility (MS) and fertility-restorer (RF) lines;<br>Ø expression of a gene for resistance to antibiotics. | |
| E-3 | Liberty Link ® | *Brassica napus* (Argentine canola rape) | BayerCropScience | Phosphinotricin tolerance | |
| E-4 | Roundup Ready ® | *Brassica napus* (canola rape) | Monsanto Company | Glyphosate tolerance | |
| E-5 | Clearfield ® | (Canola rape) | BASF Corporation | Non-GMO, imazamox tolerance | |
| E-6 | Optimum ™ GAT ™ | *Glycine max* L. (soya bean) | Pioneer Hi-Bred International, Inc | Glyphosate and ALS herbicide tolerance | |
| E-7 | Roundup Ready ® | *Glycine max* L. (soya bean) | Monsanto Company | Glyphosate tolerance | |
| E-8 | Roundup RReady2Yiel ™ | *Glycine max* L. (soya bean) | Monsanto Company | Glyphosate tolerance | |
| E-9 | STS ® | *Glycine max* L. (soya bean) | DuPont | Sulfonylurea tolerance | |
| E-10 | YIELD GARD ® | *Glycine max* L. (soya bean) | Monsanto Company | | |
| E-11 | AFD ® | *Gossypium hirsutum* L. (cotton) | Bayer CropScience | The lines include, for example, AFD5062LL, AFD5064F, AFD 5065B2F; AFD seed is available in a wide range of varieties with integrated technology such as, for example, the Bollgard ®, Bollgard II, Roundup Ready, Roundup Ready Flex and LibertyLink ®technologies | |
| E-12 | Bollgard II ® | *Gossypium hirsutum* L. (cotton) | Monsanto Company | MON 15985 event: Cry2(A)b1; Cry1A(c) | |
| E-13 | Bollgard ® | *Gossypium hirsutum* L. (cotton) | Monsanto Company | Cry1Ac | |
| E-14 | FiberMax ® | *Gossypium hirsutum* L. (cotton) | Bayer CropScience | | |
| E-15 | Liberty Link ® | *Gossypium hirsutum* L. (cotton) | Bayer CropScience | Phosphinotricin tolerance | |
| E-16 | Nucotn 33B | *Gossypium hirsutum* L. (cotton) | Delta Pine and Land | Bt toxin in the lines from Delta Pine: Cry1Ac | |

TABLE E-continued

Non-exhaustive list of transgenic events and traits and their trade names.

| No. | Trade name | Plant | Company | Genetically modified properties | Additional information |
|---|---|---|---|---|---|
| E-17 | Nucotn 35B | *Gossypium hirsutum* L. (cotton) | Delta Pine and Land | Bt toxin in the lines from Delta Pine: Cry1Ac | |
| E-18 | Nucotn ® | *Gossypium hirsutum* L. (cotton) | Delta Pine and Land | Bt toxin in the lines from Delta Pine | |
| E-19 | PhytoGen ™ | *Gossypium hirsutum* L. (cotton) | PhytoGen Seed Company, Dow AgroSciences LLC | Comprises varieties which contain, for example, Roundup Ready flex, Widestrike | |
| E-20 | Roundup Ready Flex ® | *Gossypium hirsutum* L. (cotton) | Monsanto Company | Glyphosate tolerance | |
| E-21 | Roundup Ready ® | *Gossypium hirsutum* L. (cotton) | Monsanto Company | Glyphosate tolerance | |
| E-22 | Widestrike ™ | *Gossypium hirsutum* L. (cotton) | Dow AgroSciences LLC | Cry1F and Cry1Ac | Monsanto/Dow |
| E-23 | YIELD GARD ® | *Gossypium hirsutum* L. (cotton) | Monsanto Company | | http://www.garstseed.com/GarstClient/Technology/agrisure.aspx |
| E-24 | Roundup Ready ® | *Medicago sativa* (alfalfa) | Monsanto Company | Glyphosate tolerance | |
| E-25 | Clearfield ® | *Oryza sativa* (rice) | BASF Corporation | Non-GMO, imazamox tolerance | |
| E-26 | NewLeaf ® | *Solanum tuberosum* L. (potato) | Monsanto Company | Resistance to infection by potato leafroll virus (PLRV) and feeding damage by the Colorado beetle *Leptinotarsa decemlineata* | |
| E-27 | NewLeaf ® | *Solanum plus tuberosum* L. (potato) | Monsanto Company | Resistance to infection by potato leafroll virus (PLRV) and feeding damage by the Colorado beetle *Leptinotarsa decemlineata* | http://www.dowagro.com/phytogen/index.htm |
| E-28 | Protecta ® | *Solanum tuberosum* L. (potato) | | | |
| E-29 | Clearfield ® | Sunflower | BASF Corporation | Non-GMO, imazamox tolerance | |
| E-30 | Roundup Ready ® | *Triticum aestivum* (wheat) | Monsanto Company | Glyphosate tolerance, NK603 | |
| E-31 | Clearfield ® | Wheat | BASF Corporation | Non-GMO, imazamox tolerance | |
| E-32 | Agrisure ® (Family) | *Zea mays* L. (maize) | Syngenta Seeds, Inc. | These include Agrisure CB/LL (BT 11 event plus phosphinotricin tolerance as the result of GA21 event); Agrisure CB/LL/RW (Bt 11 event, modified synthetic Cry3A gene, phosphinotricin tolerance as the result of GA21 event); Agrisure GT (glyphosate tolerance); Agrisure GT/CB/LL(glyphosate tolerance and phosphinotricin tolerance as the result of GA21 event, Bt 11 event); Agrisure 3000GT (CB/LL/RW/GT: glyphosate and phosphinotricin tolerance as the result of GA21 event; Bt 11 event, modified synthetic Cry3A gene); Agrisure GT/RW (glyphosate tolerance, modified synthetic Cry3A gene); Agrisure RW (modified synthetic Cry3A gene); future traits | |
| E-33 | BiteGard ® | *Zea mays* L. (maize) | Novartis Seeds | cry1A(b) gene | |
| E-34 | Bt-Xtra ® | *Zea mays* L. (maize) | DEKALB Genetics Corporation | cry1Ac gene | |
| E-35 | Clearfield ® | *Zea mays* L. (maize) | BASF Corporation | Non-GMO, imazamox tolerance | |
| E-36 | Herculex ® (Familie) | *Zea mays* L. (maize) | Dow Agro Sciences LLC | | |
| E-37 | IMI ® | *Zea mays* L. (maize) | DuPont | Imidazolinone tolerance | |
| E-38 | KnockOut ® | *Zea mays* L. (maize) | Syngenta Seeds, Inc. | SYN-EV176-9: cry1A(b) gene | |
| E-39 | Mavera ® | *Zea mays* L. (maize) | Renessen LLC | High lysine | http://www.dowagro.com/widestrike/ |
| E-40 | NatureGard ® | *Zea mays* L. (maize) | Mycogen | cry1A(b) gene | |
| E-41 | Roundup Ready ® | *Zea mays* L. (maize) | Monsanto Company | Glyphosate tolerance | http://www.starlinkcom.com/starlinkcorn.htm |

TABLE E-continued

Non-exhaustive list of transgenic events and traits and their trade names.

| No. | Trade name | Plant | Company | Genetically modified properties | Additional information |
|---|---|---|---|---|---|
| E-42 | Roundup Ready ® 2 | Zea mays L. (maize) | Monsanto Company | Glyphosate tolerance | |
| E-43 | SmartStax | Zea mays L. (maize) | Monsanto Company | Combination of eight genes | |
| E-44 | StarLink ® | Zea mays L. (maize) | Aventis CropScience -> Bayer CropScience | Cry9c gene | |
| E-45 | STS ® | Zea mays L. (maize) | DuPont | Sulfonylurea tolerance | |
| E-46 | YIELD GARD ® | Zea mays L. (maize) | Monsanto Company | Mon810, Cry1Ab1; resistance to the European Corn Borer | http://www.dowagro.com/ herculex/about/herculexfamily/ |
| E-47 | YieldGard ® Plus | Zea mays L. (maize) | Monsanto Company | Mon810 × Mon863, dual resistance to European Corn Borer and corn rootworm | |
| E-48 | YieldGard ® Rootworm | Zea mays L. (maize) | Monsanto Company | Mon863, Cry3Bb1, resistance to corn rootworm | |
| E-49 | YieldGard ® VT | Zea mays L. (Maize) | Monsanto Company | Stacked traits | |
| E-50 | YieldMaker ™ | Zea mays L. (Maize) | DEKALB Genetics Corporation | Contains Roundup Ready 2 technology, YieldGard VT, YieldGard Corn Borer, YieldGard Rootworm and YieldGard Plus | |

Transgenic crop plants that can be treated in accordance with the invention are preferably plants which comprise transformation events (transformation-integration events) or a combination of transformation events (transformation-integration events) and which, for example, are listed in the databases for various national or regional registration authorities, including event 1143-14A (cotton, insect control, not filed, described in WO2006/128569); event 1143-51B (cotton, insect control, not filed, described in WO2006/128570); event 1445 (cotton, herbicide tolerance, not filed, described in US2002120964 or WO2002/034946); event 17053 (rice, herbicide tolerance, filed as PTA-9843, described in WO2010/117737); event 17314 (rice, herbicide tolerance, filed as PTA-9844, described in WO2010/117735); event 281-24-236 (cotton, insect control—herbicide tolerance, filed as PTA-6233, described in WO2005/103266 or US2005216969); event 3006-210-23 (cotton, insect control—herbicide tolerance, filed as PTA-6233, described in US2007143876 or WO2005/103266); event 3272 (maize, quality trait, filed as PTA-9972, described in WO2006098952 or US2006230473); event 40416 (maize, insect control—herbicide tolerance, filed as ATCC PTA-11508, described in WO2011/075593); event 43A47 (maize, insect control—herbicide tolerance, filed as ATCC PTA-11509, described in WO2011/075595); event 5307 (maize, insect control, filed as ATCC PTA-9561, described in WO2010/077816); event ASR-368 [bent grass, herbicide tolerance, filed as ATCC PTA-4816, described in US2006162007 or WO2004053062]; event B16 (maize, herbicide tolerance, not filed, described in US2003126634); event BPS-CV127-9 (soya bean, herbicide tolerance, filed as NCIMB No. 41603, described in WO2010/080829); event CE43-67B (cotton, insect control, filed as DSM ACC2724, described in US2009217423 or WO2006/128573); event CE44-69D (cotton, insect control, not filed, described in US20100024077); event CE44-69D (cotton, insect control, not filed, described in WO2006/128571); event CE46-02A (cotton, insect control, not filed, described in WO2006/128572); event COT102 (cotton, insect control, not filed, described in US2006130175 or WO2004039986); event COT202 (cotton, insect control, not filed, described in US2007067868 or WO2005054479); event COT203 (cotton, insect control, not filed, described in WO2005/054480); event DAS40278 (maize, herbicide tolerance, filed as ATCC PTA-10244, described in WO2011/022469); event DAS-59122-7 (maize, insect control—herbicide tolerance, filed as ATCC PTA 11384, described in US2006070139); event DAS-59132 (maize, insect control—herbicide tolerance, not filed, described in WO2009/100188); event DAS68416 (soya bean, herbicide tolerance, filed as ATCC PTA-10442, described in WO2011/066384 or WO2011/066360); event DP-098140-6 (maize, herbicide tolerance, filed as ATCC PTA-8296, described in US2009137395 or WO2008/112019); event DP-305423-1 (soya bean, quality trait, not filed, described in US2008312082 or WO2008/054747); event DP-32138-1 (maize, hybrid system, filed as ATCC PTA-9158, described in US20090210970 or WO2009/103049); event DP-356043-5 (soya bean, herbicide tolerance, filed as ATCC PTA-8287, described in US20100184079 or WO2008/002872); event EE-1 (aubergine, insect control, not filed, described in WO2007/091277); event FI117 (maize, herbicide tolerance, filed as ATCC 209031, described in US2006059581 or WO1998/044140); event GA21 (maize, herbicide tolerance, filed as ATCC 209033, described in US2005086719 or WO1998/044140); event GG25 (maize, herbicide tolerance, filed as ATCC 209032, described in US2005188434 or WO1998/044140); event GHB119 (cotton, insect control—herbicide tolerance, filed as ATCC PTA-8398, described in WO2008/151780); event GHB614 (cotton, herbicide tolerance, filed as ATCC PTA-6878, described in US2010050282 or WO2007/017186); event GJ11 (maize, herbicide tolerance, filed as ATCC 209030, described in US2005188434 or WO1998/044140); event GM RZ13 (sugar beet, virus resistance, filed as NCIMB-41601, described in WO2010/076212); event H7-1 (sugar beet, herbicide tolerance, filed as NCIMB 41158 or NCIMB 41159, described in US2004172669 or WO2004/074492); event JOPLIN1 (wheat, fungus resistance, not filed, described in US2008064032); event LL27 (soya bean, herbicide tolerance, filed as NCIMB41658, described in WO2006/108674 or US2008320616); event LL55 (soya bean, herbicide tolerance, filed as NCIMB 41660, described in WO2006/108675 or US2008196127); event LLcotton25 (cotton, herbicide tolerance, filed as ATCC PTA-3343, described in WO2003013224 or US2003097687); event LLRICE06 (rice, herbicide tolerance, filed as ATCC-23352, described in US6468747 or WO2000/026345); event LLRICE601 (rice, herbicide tolerance, filed as ATCC PTA-2600, described in US20082289060 or WO2000/026356); event LY038 (maize, quality trait, filed as ATCC PTA-5623, described in US2007028322 or WO2005061720); event MIR162 (maize, insect control, filed as PTA-8166, described in US2009300784 or WO2007/142840); event MIR604 (maize, insect control, not filed, described in US2008167456 or WO2005103301); event MON15985 (cotton, insect control, filed as ATCC PTA-2516, described in US2004-250317 or WO2002/100163); event MON810 (maize, insect control, not filed, described in US2002102582); event MON863 (maize, insect control, filed as ATCC PTA-2605, described in WO2004/011601 or US2006095986); event MON87427 (maize, pollination control, filed as ATCC PTA-7899, described in WO2011/062904); event MON87460 (maize, stress tolerance, filed as ATCC PTA-8910, described in WO2009/111263 or US20110138504); event MON87701 (soya bean, insect control, filed as ATCC PTA-8194, described in US2009130071 or WO2009/064652); event MON87705 (soya bean, quality trait—herbicide tolerance, filed as ATCC PTA-9241, described in US20100080887 or WO2010/037016); event MON87708 (soya bean, herbicide tolerance, filed as ATCC PTA9670, described in WO2011/034704); event MON87754 (soya bean, quality feature, filed as ATCC PTA-9385, described in WO2010/024976); event MON87769 (soya bean, quality trait, filed as ATCC PTA-8911, described in US20110067141 or WO2009/102873); event MON88017 (maize, insect control—herbicide tolerance, filed as ATCC PTA-5582, described in US2008028482 or WO2005/059103); event MON88913 (cotton, herbicide tolerance, filed as ATCC PTA-4854, described in WO2004/072235 or US2006059590); event MON89034 (maize, insect control, filed as ATCC PTA-7455, described in WO2007/140256 or US2008260932); event MON89788 (soya bean, herbicide tolerance, filed as ATCC PTA-6708, described in US2006282915 or WO2006/130436); event MS11 (oilseed rape, pollination control—herbicide tolerance, filed as ATCC PTA-850 or PTA-2485, described in WO2001/031042); event MS8 (oilseed rape, pollination control—herbicide tolerance, filed as ATCC PTA-730, described in WO2001/041558 or US2003188347); event NK603 (maize, herbicide tolerance, filed as ATCC PTA-2478, described in US2007-292854); event PE-7 (rice, insect control, not filed, described in WO2008/114282); event RF3 (oilseed rape, pollination control—herbicide tolerance, filed as ATCC PTA-730, described in WO2001/041558 or US2003188347); event RT73 (oilseed rape, herbicide tolerance, not filed, described in WO2002/036831 or US2008070260); event T227-1 (sugar beet, herbicide tolerance, not filed, described in WO2002/44407 or US2009265817); event T25 (maize, herbicide tolerance, not filed, described in US2001029014 or WO2001/051654); event T304-40 (cotton, insect control—herbicide tolerance, filed as ATCC PTA-8171, described in US2010077501 or WO2008/122406); event T342-142 (cotton, insect control, not filed, described in WO2006/128568); event TC1507 (maize, insect control—herbicide tolerance, not filed, described in US2005039226 or WO2004/099447); event VIP1034 (maize, insect control—herbicide tolerance, filed as ATCC PTA-3925, described in WO2003/052073); event 32316 (maize, insect control—herbicide tolerance, filed as PTA-11507, described in WO2011/084632); event 4114 (maize, insect control—herbicide tolerance, filed as PTA-11506, described in WO2011/084621).

The plants listed can be treated in accordance with the invention in a particularly advantageous manner with the inventive active ingredient mixture. The preferred ranges stated above for the mixtures also apply to the treatment of these plants. Particular emphasis is given to the treatment of plants with the mixtures specifically mentioned in the present text.

The control of animal pests, especially of nematodes, by treating the seed of plants has been known for a long time and is the subject of continual improvements. However, in the treatment of seed, a number of problems are encountered which cannot always be resolved in a satisfactory manner. Thus, it is desirable to develop methods for protecting the seed and the germinating plant which at least significantly reduce, or make superfluous, the additional application of crop protection agents after sowing or after the emergence of the plants. It is additionally desirable to optimize the amount of active ingredient employed in such a way as to provide maximum protection for the seed and the germinating plant from attack by animal pests, especially nematodes, but without damaging the plant itself by the active ingredient used. In particular, methods for the treatment of seed should also take into consideration the intrinsic insecticidal properties of transgenic plants in order to achieve optimum protection of the seed and the germinating plant with a minimum of crop protection agents being employed.

The present invention therefore also relates especially to a method for the protection of seed and germinating plants from attack by animal pests, especially by nematodes, and also to a method for increasing yields, by treating the seed with an inventive composition.

The invention likewise relates to the use of the inventive compositions for the treatment of seed for protecting the seed and the germinating plant from animal pests, especially from nematodes, and also for increasing yields.

The invention further relates to seed which has been treated with an inventive composition for protection from animal pests, especially nematodes.

One of the advantages of the present invention is that the particular systemic properties of the inventive compositions mean that treatment of the seed with these compositions not only protects the seed itself, but also the resulting plants after emergence, from animal pests, especially nematodes. In this manner, the immediate treatment of the crop at the time of sowing or shortly thereafter can be dispensed with.

It is also considered to be advantageous that the inventive mixtures can also be used for transgenic seed in particular.

Formulations

The active ingredient combinations can be converted to the customary formulations such as solutions, emulsions, wettable powders, suspensions, powders, dusts, pastes, soluble powders, granules, suspension-emulsion concentrates, natural and synthetic materials impregnated with active ingredient, and microencapsulations in polymeric materials, for the foliar and soil applications.

These formulations are produced in a known manner, for example by mixing the active ingredients with extenders, that is, liquid solvents and/or solid carriers, optionally with the use of surfactants, that is, emulsifiers and/or dispersants, and/or foam formers.

If the extender used comprises water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and water.

Suitable solid carriers are:
for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

The formulations generally contain between 0.1 and 95 wt % of active ingredient, preferably between 0.5 and 90%.

The inventive active ingredient combinations may be present in commercially standard formulations and in the use forms, prepared from these formulations, as a mixture with other active ingredients, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, etc.

Mixing with other known active ingredients such as herbicides or with fertilizers and growth regulators is also possible.

When used as insecticides, the inventive active ingredient combinations may additionally be present in their commercially available formulations and in the use forms, prepared from these formulations, as a mixture with synergists. Synergists are compounds which enhance the action of the active ingredients, without it being necessary for the synergist added to be active itself.

The active ingredient content of the use forms prepared from the commercially available formulations may vary within wide limits. The active ingredient concentration of the use forms may be from 0.0000001 to 95 wt % of active ingredient, preferably between 0.0001 and 50 wt %.

The compounds are employed in a customary manner appropriate for the use forms.

Use Forms

When the active ingredients of the invention are used for controlling animal pests, more particularly nematodes, the application rates may be varied within a relatively wide range, depending on the mode of application. The application rate of the active ingredients of the invention
when treating parts of plants, such as leaves, is as follows: from 0.1 to 10 000 g/ha, preferably from 10 to 1000 g/ha, more preferably from 50 to 300 g/ha (if applied by watering or dripping, the application rate may even be reduced, especially if inert substrates such as rock wool or perlite are used);
in the treatment of seed is as follows: from 2 to 200 g per 100 kg of seed, preferably from 3 to 150 g per 100 kg of seed, more preferably from 2.5 to 25 g per 100 kg of seed, very preferably from 2.5 to 12.5 g per 100 kg of seed;
for soil treatment is as follows: from 0.1 to 10 000 g/ha, preferably from 1 to 5000 g/ha.

These application rates are given only by way of example and without limitation for the purposes of the invention.

The active ingredients and/or compositions of the invention can therefore be used to protect plants, within a certain period of time after treatment, against infestation by animal pests, more particularly nematodes. The period of time within which protection of the plant is brought about extends in general over 1 to 28 days, preferably over 1 to 14 days, more preferably over 1 to 10 days, very preferably over 1 to 7 days after the treatment of the plants with the active ingredients, or to up to 200 days after seed treatment.

Foliar Applications

Foliar application is understood to mean the inventive treatment of the plants and plant parts with the active ingredients directly or by action on the environment, habitat or storage space thereof by the customary treatment methods, for example by dipping, spraying, vaporizing, nebulizing, scattering, painting and injecting. Plant parts are understood to mean all above-ground and below-ground parts and organs of the plants, such as shoot, leaf, flower and root, examples including leaves, needles, stems, stalks, flowers, fruit-bodies, fruits and seeds, and also roots, tubers and rhizomes. The plant parts also include harvested plants and vegetative and generative propagation material, for example seedlings, tubers, rhizomes, runners and seeds.

Soil Application

Soil application is understood to mean the control of insects and/or spider mites and/or nematodes by drenching pesticides onto the soil, incorporating them into the soil and in irrigation systems as droplet application onto the soil. Alternatively, the inventive active ingredient combinations can be introduced into the site of the plants in solid form (for example in the form of granules). In the case of paddy rice crops, this may also be accomplished by metering the inventive active ingredient combinations in a solid application form (for example as a granule) into a flooded paddy field.

The invention relates to these application forms to natural (soil) or artificial substrates (for example rock wool, glass wool, quartz sand, pebbles, expanded clay, vermiculite), outdoors or in closed systems (e.g. greenhouses or under film cover) and in annual (e.g. vegetables, potatoes, cotton, beet, ornamental plants) or perennial crops (e.g. citrus plants, fruit, tropical crops, spices, nuts, vines, conifers and ornamental plants). It is additionally possible to deploy the active ingredients by the ultra-low-volume method or to inject the active ingredient formulation or the active ingredient itself into the soil.

Seed Treatment

The inventive active ingredient combinations are suitable especially for protection of seed of any plant variety which is used in agriculture, in greenhouses, in forests or in horticulture from the aforementioned animal pests, especially from nematodes. More particularly, the seed is that of cereals (such as wheat, barley, rye, millet and sorghum, and oats), maize, cotton, soya, rice, potatoes, sunflower, beans, coffee, beet (e.g. sugar beet and fodder beet), peanut, vegetables (such as tomato, cucumber, onions and lettuce), lawns and ornamental plants. Of particular significance is the treatment of the seed of cereals (such as wheat, barley, rye and oats), maize and rice, and the treatment of cotton and soya seed.

In the context of the present invention, the inventive composition is applied on its own or in a suitable formulation to the seed. Preferably, the seed is treated in a state in which it is sufficiently stable that the treatment does not cause any damage. In general, treatment of the seed may take place at any point in time between harvesting and sowing. Typically, the seed used has been separated from the plant and freed from cobs, shells, stalks, coats, hairs or the flesh of the fruits. For example, it is possible to use seed which has been harvested, cleaned and dried to a moisture content of less than 15 wt %. Alternatively, it is also possible to use seed which, after drying, has been treated, for example, with water and then dried again.

When treating the seed, it generally has to be ensured that the amount of the inventive composition applied to the seed and/or the amount of further additives is selected such that the germination of the seed is not adversely affected, and that the resulting plant is not damaged. This must be borne in mind in particular in the case of active ingredients which may exhibit phytotoxic effects at certain application rates.

The inventive active ingredient combinations/compositions can be applied directly, i.e. without comprising any further components and without having been diluted. In general, it is preferable to apply the compositions to the seed in the form of a suitable formulation. Suitable formulations and methods for the treatment of seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active ingredient combinations usable in accordance with the invention can be converted to the customary seed dressing product formulations such as solutions, emulsions, suspensions, powders, foams, slurries and other coating compositions for seed, and ULV formulations.

These formulations are prepared in the known manner by mixing the active ingredients or active ingredient combinations with customary additives, for example customary extenders and also solvents or diluents, dyes, wetters, dispersants, emulsifiers, antifoams, preservatives, secondary thickeners, adhesives, gibberellins, and also water.

The colorants which may be present in the seed dressing product formulations usable in accordance with the invention are all colorants which are customary for such purposes. Both pigments, which are sparingly soluble in water, and colorants, which are soluble in water, may be used. Examples of dyes include those known by the names Rhodamine B, C.I. Pigment Red 112 and C.I. Solvent Red 1.

The wetters which may be present in the seed dressing product formulations usable in accordance with the invention are all substances which are conventionally used for the formulation of active agrochemical ingredients and for promoting wetting. Alkylnaphthalenesulfonates, such as diisopropyl- or diisobutylnaphthalenesulfonates, can be used with preference.

Useful dispersants and/or emulsifiers which may be present in the seed dressing product formulations usable in accordance with the invention are all nonionic, anionic and cationic dispersants which are conventionally used for the formulation of active agrochemical ingredients. Nonionic or anionic dispersants or mixtures of nonionic or anionic dispersants can be used with preference. Suitable nonionic dispersants include, in particular, ethylene oxide/propylene oxide block polymers, alkylphenol polyglycol ethers and tristryrylphenol polyglycol ethers, and their phosphated or sulfated derivatives. Suitable anionic dispersants are, in particular, lignosulfonates, polyacrylic acid salts and arylsulfonate/formaldehyde condensates.

The antifoams which may be present in the seed dressing product formulations usable in accordance with the invention are all foam-suppressing substances conventionally used for the formulation of active agrochemical ingredients. Silicone antifoams and magnesium stearate can be used with preference.

The preservatives which may be present in the seed dressing product formulations usable in accordance with the invention are all substances which can be employed in agrochemical compositions for such purposes. Examples include dichlorophen and benzyl alcohol hemiformal.

The secondary thickeners which may be present in the seed dressing product formulations usable in accordance with the invention are all substances which can be employed in agrochemical compositions for such purposes. Cellulose derivatives, acrylic acid derivatives, xanthan, modified clays and finely divided silica are preferred.

The adhesives which may be present in the seed dressing product formulations usable in accordance with the invention are all customary binders which can be employed in seed dressing products. Preference is given to polyvinylpyrrolidone, polyvinyl acetate, polyvinyl alcohol and tylose.

The gibberellins which may be present in the seed dressing product formulations usable in accordance with the invention are preferably the gibberellins A1, A3 (=gibberellic acid), A4 and A7, particular preference being given to using gibberellic acid. The gibberellins are known (cf. R. Wegler "Chemie der Pflanzenschutz- and Schadlingsbekampfungsmittel" [Chemistry of Plant Protectants and Pesticides], Vol. 2, Springer Verlag, 1970, pp. 401-412).

The seed dressing product formulations usable in accordance with the invention can be employed either directly or after preceding dilution with water for the treatment of a wide range of seeds. For instance, the concentrates or the formulations obtainable therefrom by dilution with water can be used to dress the seed of cereals, such as wheat, barley, rye, oats and triticale, and the seed of maize, rice, rape, peas, beans, cotton, soya, sunflowers and beet, or else a wide variety of different vegetable seeds. The seed dressing product formulations usable in accordance with the invention or the dilute preparations thereof can also be used to dress seed of transgenic plants. In this context, additional synergistic effects may also occur as a consequence of the interaction with the substances formed by expression.

Useful apparatus which can be used to treat seed with the seed dressing product formulations usable in accordance with the invention, or with the preparations prepared therefrom by addition of water, is all mixing apparatus which can typically be used to dress seed. Specifically, the seed dressing procedure is to place the seed into a mixer, add the amount of seed dressing product formulation desired in each case, either as such or after preceding dilution with water, and mix until the formulation has been distributed homogeneously on the seed. If appropriate, this is followed by a drying process.

The application rate of the seed dressing product formulations usable in accordance with the invention can be varied within a relatively wide range. It is guided by the particular content of the active ingredients in the formulations and by the seed. The application rates of the active ingredient combinations are generally between 0.001 and 50 g per kilogram of seed, preferably between 0.01 and 25 g per kilogram of seed.

Calculation Formula for the Mortality of a Combination of Two Active Ingredients The anticipated effect of a given combination of two active ingredients may be calculated (cf. Colby, S. R., "Calculating Synergistic and Antagonistic Responses of Herbicide Combinations", Weeds 15, pages 20-22, 1967) as follows:

if

X is the mortality, expressed in % of the untreated control, when active ingredient A is used in an application rate of m ppm, or m g/ha Y is the mortality, expressed in % of the untreated control, when active ingredient B is used in an application rate of n ppm, or n g/ha E is the mortality, expressed in % of the untreated control, when active ingredients A and B are used at application rates of m and n ppm or of m and n g/ha, then $$E = X + Y - \frac{X \cdot Y}{100}.$$

If the actual insecticide mortality is greater than calculated, then the combination is superadditive in its kill—that is, there is a synergistic effect. In this case the mortality actually observed must be greater than the value for the expected mortality (E) calculated on the basis of the formula given above.

Example 1

*Myzus* Test (Spray Treatment)

Solvent: 78 parts by weight of acetone 1.5 parts by weight of dimethylformamide

Emulsifier: 0.5 part by weight of alkylaryl polyglycol ether

A suitable preparation of active ingredient is prepared by mixing one part by weight of active ingredient with the stated amounts of solvent and emulsifier and diluting the concentrate with emulsifier-containing water to the desired concentration. A suitable suspension of biological agent is prepared by dissolving the cells, spores or viruses in emulsifier-containing water in the desired concentration.

Chinese cabbage (*Brassica pekinensis*) leaf disks infested by all stages of the green peach aphid (*Myzus persicae*) are sprayed with an active ingredient and/or biological agent preparation in the desired concentration.

After the desired time, the effect in % is ascertained. Here, 100% means that all of the aphids have been killed; 0% means that no aphids have been killed. The mortality figures determined are used for calculation according to the Colby formula (see sheet 1).

In this test, the following combination of fluopyram with a further active ingredient or with a biological agent in accordance with the present specification gave a synergistically boosted activity in comparison to the substances employed individually:

TABLE 1

Myzus persicae test

| Active ingredient/biological agents | Concentration g ai/ha | Mortality in % after $1^d$ | |
|---|---|---|---|
| Fluopyram | 1000 | 0 | |
|  | 500 | 0 | |
| Imicyafos | 67.5 | 0 | |
| Fluopyram + imicyafos |  | found* | calc.** |
|  | 1000 + 67.5 | 100 | 0 |
| Pyrethrum | 100 | 80 | |
| Fluopyram + pyrethrum |  | found* | calc.** |
|  | 1000 + 100 | 100 | 80 |
| Fluensulfone | 2000 | 0 | |
| Fluopyram + fluensulfone |  | found* | calc.** |
|  | 500 + 2000 | 90 | 0 |
| *Paecilomyces lilacinus* strain 251 | 5000 | 0 | |
| Fluopyram + *Paecilomyces lilacinus* strain 251 |  | found* | calc.** |
|  | 1000 + 5000 | 70 | 0 |
| *Bacillus amyloliquefaciens* strain FZB 42 | 2000 | 0 | |
| Fluopyram + *Bacillus amyloliquefaciens* |  | found* | calc.** |
|  | 1000 + 2000 | 90 | 0 |
| *Cydia pomonella* granulosis virus (CpGV) | 1000 | 0 | |
| Fluopyram + *Cydia pomonella* granulosis virus (CpGV) |  | found* | calc.** |
|  | 1000 + 1000 | 70 | 0 |
| Fluopyram | 1000 | 0 | |
|  | 500 | 0 | |

TABLE 1-continued

| Myzus persicae test | | | |
|---|---|---|---|
| Active ingredient/biological agents | Concentration g ai/ha | Mortality in % after 1$^d$ | |
| *Bacillus thuringiensis* subsp. *tenebrionis* | 1000 | 0 | |
| Fluopyram + *Bacillus thuringiensis* subsp. *tenebrionis* | | found* | calc.** |
| | 1000 + 1000 | 80 | 0 |
| Azadirachtin | 100 | 100 | 0 |
| Fluopyram + azadirachtin | | found* | calc.** |
| | 1000 + 100 | 70 | 0 |
| *Metschnikowia fructicola* | 1000 | 0 | |
| Fluopyram + *Metschnikowia fructicola* | | found* | calc.** |
| | 500 + 1000 | 90 | 0 |

*found = insecticidal action found,
**calc. = action calculated by the Colby formula

Example 2

*Spodoptera frugiperda* Test (Spray Treatment)
Solvent: 78.0 parts by weight of acetone
1.5 parts by weight of dimethylformamide
Emulsifier: 0.5 part by weight of alkylaryl polyglycol ether A suitable preparation of active ingredient is prepared by mixing one part by weight of active ingredient with the stated amounts of solvent and emulsifier and diluting the concentrate with emulsifier-containing water to the desired concentration. Maize (*Zea mays*; corn) leaf disks are sprayed with an active ingredient preparation of the desired concentration and, after drying off, are populated with caterpillars of the army worm (*Spodoptera frugiperda*).

After the desired time, the effect in % is ascertained. Here, 100% means that all of the caterpillars have been killed, 0% means that no caterpillar has been killed. The mortality figures determined are used for calculation according to the Colby formula (see sheet 1).

In this test, the following combination of fluopyram and a further active ingredient in accordance with the present specification gave a synergistically boosted activity in comparison to the active ingredients employed individually:

TABLE 2

| Spodoptera frugiperda test | | | |
|---|---|---|---|
| Active ingredient/ biological agents | Concentration g ai/ha | Mortality in % after 2d | |
| Fluopyram | 1000 | 0 | |
| Pyrethrum | 100 | 33 | |
| Fluopyram + pyrethrum | | found* | calc.** |
| | 1000 + 100 | 50 | 33 |

*found = insecticidal action found,
**calc. = action calculated by the Colby formula

Example 3

Seed Treatment—Cotton Emergence Test

Seed of cotton (*Gossypium hirsutum*) is mixed with the desired amount of active ingredient and spores and also water. After drying, 25 seed grains in each case are sown in pots filled with sandy loam.

After 2 days, the effect in % is ascertained on the basis of the cotton plants that have emerged.

The following combinations of fluopyram and biological agents gave a better emergence rate in comparison to the substances employed individually and to the untreated control:

TABLE 3

| Cotton emergence | | |
|---|---|---|
| Active ingredient/biological agents | Concentration g ai/kg seed | Emergence in % in comparison to untreated control |
| Control (untreated seed) | | 100 |
| Fluopyram | 1 | 133 |
| | 0.5 | 100 |
| *Bacillus subtilis* strain GB 03 | 0.078 | 158 |
| Fluopyram + *B. subtilis* strain GB 03 | 0.5 + 0.078 | 288 |
| *Bacillus amyloliquefaciens* strain FZB 42 | 0.15 | 163 |
| | 0.075 | 158 |
| Fluopyram + *B. amyloliquefaciens* strain FZB 42 | 1.0 + 0.15 | 225 |
| | 0.5 + 0.075 | 221 |

*found = insecticidal action found,
**calc. = action calculated by the Colby formula

Example 4

*Meloidogyne incognita* Test
Solvent: 125.0 parts by weight of acetone

A suitable preparation of active ingredient is prepared by mixing one part by weight of active ingredient with the stated amounts of solvent and diluting the concentrate with water to the desired concentration. A spore suspension is prepared by diluting the spores with water to the desired concentration.

Vessels are filled with sand, active ingredient solution, *Meloidogyne incognita* egg-and-larvae suspension, and lettuce seeds. The lettuce seeds germinate and the seedlings develop. The galls develop on the roots.

After the desired time, the nematicidal effect is determined on the basis of gall formation in %. Here, 100% means that no galls have been found; 0% means that the number of galls on the treated plants corresponds to the untreated control. The figures ascertained are used for calculation according to the Colby formula (see sheet 1).

In this test, the following combination of fluopyram and biological agents in accordance with the present specification gave a synergistically boosted activity in comparison to the active ingredients employed individually:

TABLE 4

| Meloidogyne incognita test | | |
|---|---|---|
| Active ingredient/biological agents | Concentration in ppm | Mortality in % after 21d |
| Fluopyram | 0.0005 | 0 |
| *Metarhizium anisopliae* strain F52 | 5 | 0 |
| Fluopyram + *M. anisopliae* strain F52 | | found* calc.** |
| | 0.0005 + 5 | 80      0 |

*found = insecticidal action found,
**calc. = action calculated by the Colby formula

Example 5

*Glycine max*—Growth Promotion in Combination with Mycorrhiza

Seed of soya beans (*Glycine max*) is mixed with the desired amount of active ingredient in water. After drying, the seeds are sown in pots filled with sand and perlite (1:1). For inoculation with arbuscular *mycorrhiza* fungi, the sand-perlite mixture is mixed beforehand with the *Mycorrhiza inoculum* (AMykor GmbH; Germany) in a concentration of 25 ml/L. The seed is covered with 3 cm of Lecaton (expanded clay).

Over the following 44 days, the plants are cultivated in a greenhouse in good growth conditions. The pots are watered with a nutrient solution (Hoagland and Amon, 1950, half-concentrated solution) with a low phosphate concentration (20 µM).

The untreated control plants are cultured without arbuscular *mycorrhiza* fungi, but under the same conditions.

The growth-promoting effect on shoot and roots is ascertained via the weight of the fresh roots of the treated plant in comparison to the untreated control.

The following combination of active ingredient and biological agents gives increased root growth in comparison to the ingredients and agents applied individually, and to the control:

TABLE 5

| Plant growth of soya bean | | |
|---|---|---|
| Active ingredient/ biological agents | Concentration mg/seed grain | Root weight in % in comparison to untreated control |
| Control | — | 100 |
| Fluopyram | 0.1 | 116.90 |
| Arbuscular mycorrhiza fungus | — | 133.21 |
| Fluopyram + arbuscular mycorrhiza fungus | 0.1 | 137.91 |

The invention claimed is:

1. An active ingredient combination comprising synergistically effective amounts of:

(I-1) N-{2-[3-chloro-5-(trifluoromethyl)-2-pyridinyl]ethyl}-2-trifluoromethylbenzamide of formula (I)

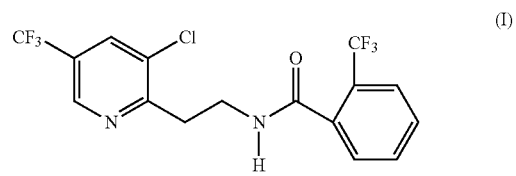

(fluopyram)
and/or an N-oxide thereof and (II) *Paecilomyces lilacinus* strain 251,
wherein the sole active components in the combination are fluopyram and *Paecilomyces lilacinus* strain 251.

2. A method for controlling one of more animal pests, comprising causing an active ingredient combination as defined in claim 1, to act on leaves, flowers, stems and/or seed of a plant to be protected, on an animal pest and/or a habitat thereof, and/or on soil.

3. A process for preparing a nematicidal composition, comprising mixing an active ingredient combination as defined in claim 1, with at least one extender and/or surfactant.

4. A composition comprising an active ingredient combination of claim 1, for controlling one or more animal pests.

5. A seed comprising an active ingredient combination as defined in claim 1.

6. A method for treating seed comprising contacting said seed with a combination as claimed in claim 1.

7. A method for treating soil and/or an artificial substrate comprising contacting said soil and/or substrate with a combination as claimed in claim 1.

8. The active ingredient combination as defined in claim 1, wherein the weight ratio of (I-1) to said *Paecilomyces lilacinus* strain 251 is 500:1 to 1:500.

9. The active ingredient combination as defined in claim 1, wherein the weight ratio of (I-1) to said *Paecilomyces lilacinus* strain 251 is 125:1 to 1:125.

10. The active ingredient combination as defined in claim 1, wherein the weight ratio of (I-1) to said *Paecilomyces lilacinus* strain 251 is 25:1 to 1:25.

11. A method for controlling nematodes, comprising contacting soil with a combination as claimed in claim 1.

* * * * *